(12) United States Patent
Chen et al.

(10) Patent No.: US 10,973,930 B2
(45) Date of Patent: Apr. 13, 2021

(54) GENERATING GABAERGIC NEURONS IN BRAINS

(71) Applicant: The Penn State Research Foundation, University Park, PA (US)

(72) Inventors: Gong Chen, State College, PA (US); Ziyuan Guo, State College, PA (US); Zheng Wu, State College, PA (US); Zifei Pei, University Park, PA (US); Yuchen Chen, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/436,275

(22) Filed: Feb. 17, 2017

(65) Prior Publication Data

US 2017/0239373 A1    Aug. 24, 2017

Related U.S. Application Data

(60) Provisional application No. 62/296,960, filed on Feb. 18, 2016.

(51) Int. Cl.
| | | |
|---|---|---|
| *A61K 48/00* | (2006.01) | |
| *A61K 31/70* | (2006.01) | |
| *A61P 25/00* | (2006.01) | |
| *C07K 14/47* | (2006.01) | |
| *A61K 9/00* | (2006.01) | |
| *A61K 38/17* | (2006.01) | |
| *C12N 15/86* | (2006.01) | |
| *A01K 67/00* | (2006.01) | |

(52) U.S. Cl.
CPC ........ *A61K 48/0058* (2013.01); *A61K 9/0085* (2013.01); *A61K 38/1709* (2013.01); *A61K 48/0075* (2013.01); *A61P 25/00* (2018.01); *C07K 14/4702* (2013.01); *C12N 15/86* (2013.01); *A01K 2227/105* (2013.01); *A01K 2267/0318* (2013.01); *C12N 2740/13043* (2013.01); *C12N 2750/14143* (2013.01); *C12N 2840/007* (2013.01)

(58) Field of Classification Search
CPC . A61K 48/0058; A61K 48/0075; A61P 25/00; C07K 14/4702; C12N 15/86; C12N 2840/007
See application file for complete search history.

(56) References Cited

U.S. PATENT DOCUMENTS

| | | | |
|---|---|---|---|
| 5,648,097 A | 7/1997 | Nuwayser | |
| 5,695,995 A | 12/1997 | Weintraub et al. | |
| 6,444,463 B1 | 9/2002 | Tapscott | |
| 6,602,680 B2 * | 8/2003 | Rubenstein et al. | |
| 6,630,486 B1 | 10/2003 | Royer | |
| 7,041,507 B1 | 5/2006 | Levesque et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,586,363 B2 | 11/2013 | Voytas et al. | |
| 8,697,359 B1 | 4/2014 | Zhang | |
| 8,771,945 B1 | 7/2014 | Zhang | |
| 8,795,965 B2 | 8/2014 | Zhang | |
| 8,871,445 B2 | 10/2014 | Cong et al. | |
| 9,260,752 B1 | 2/2016 | May et al. | |
| 9,410,198 B2 | 8/2016 | May et al. | |
| 9,717,804 B2 | 8/2017 | Chen et al. | |
| 9,725,714 B2 | 8/2017 | May et al. | |
| 9,738,908 B2 | 8/2017 | Wu | |
| 9,803,194 B2 | 10/2017 | May et al. | |
| 9,809,814 B1 | 11/2017 | May et al. | |
| 2002/0187951 A1 * | 12/2002 | Aebischer | C07K 14/4756 514/44 R |
| 2011/0223635 A1 | 9/2011 | Deisseroth et al. | |
| 2012/0040393 A1 * | 2/2012 | Zhang et al. | |
| 2012/0301446 A1 * | 11/2012 | Zhu | C07K 14/08 424/93.7 |
| 2013/0022583 A1 | 1/2013 | Wernig et al. | |
| 2013/0095118 A1 | 4/2013 | Smith et al. | |
| 2014/0024599 A1 | 1/2014 | Chen et al. | |
| 2015/0250900 A1 | 9/2015 | Chen et al. | |
| 2015/0283065 A1 | 10/2015 | Frey, II et al. | |
| 2015/0335708 A1 | 11/2015 | Froelich et al. | |

(Continued)

FOREIGN PATENT DOCUMENTS

| | | |
|---|---|---|
| WO | WO 2005/021704 | 3/2005 |
| WO | WO 2008/083931 | 7/2008 |

(Continued)

OTHER PUBLICATIONS

Henrich et al. Methods in Molecular Biol, Ed Richard Miller, 2012;814:485-98.*
Sizemore et al. J Neurophysiol Feb 17, 2016;115: 2124-2146, 2016.*
Shin et al. Stem Cell Rev Rep 2012;8:513-31.*
Schuster et al. Front Neuroanat 2014;8-42:1-14.*
Guncova et al. The neurodegenerative process in a neurotoxic rat model and in patients with Huntington's disease: Histopathological parallels and differences. Acta Histochemica 113:783-792, (Year: 2011).*
Ivkovic et al. Expression of the striatal DARPP-32/ARPP-21 phenotype in GABAergic neurons requires neurotrophins in vivo and in vitro. J. Neuroscience 19:5409-5419, (Year: 1999).*

(Continued)

*Primary Examiner* — Quang Nguyen
(74) *Attorney, Agent, or Firm* — Fish & Richardson P.C.

(57) ABSTRACT

This document provides methods and materials for generating GABAergic neurons in brains. For example, methods and materials for using nucleic acid encoding a NeuroD1 polypeptide and nucleic acid encoding a Dlx2 polypeptide to trigger glial cells (e.g., NG2 glial cells or astrocytes) within the brain (e.g., striatum) into forming GABAergic neurons (e.g., neurons resembling medium spiny neurons such as DARPP32-positive GABAergic neurons) that are functionally integrated into the brain of a living mammal (e.g., a human) are provided.

11 Claims, 16 Drawing Sheets

Specification includes a Sequence Listing.

(56) References Cited

U.S. PATENT DOCUMENTS

| | | |
|---|---|---|
| 2017/0035839 A1 | 2/2017 | Miller et al. |
| 2017/0101622 A1 | 4/2017 | Ahlfors et al. |
| 2017/0152528 A1 | 6/2017 | Zhang |
| 2017/0224843 A1 | 8/2017 | Deglon et al. |
| 2017/0304463 A1 | 10/2017 | Chen et al. |
| 2018/0087052 A1 | 3/2018 | Hung et al. |
| 2019/0055552 A1 | 2/2019 | Davidson et al. |
| 2019/0153412 A1 | 5/2019 | Zhang et al. |

FOREIGN PATENT DOCUMENTS

| | | |
|---|---|---|
| WO | WO 2010/053522 | 5/2010 |
| WO | WO 2011/050476 | 5/2011 |
| WO | WO 2011/072246 | 6/2011 |
| WO | WO 2011/097181 | 8/2011 |
| WO | WO 2012/010675 | 1/2012 |
| WO | WO 2014/015261 | 1/2014 |
| WO | WO 2014/153230 | 9/2014 |
| WO | WO 2015/060722 | 4/2015 |
| WO | WO 2015/069736 | 5/2015 |
| WO | WO 2015/131788 | 9/2015 |
| WO | WO 2017/143207 | 8/2017 |
| WO | WO 2019/094694 | 5/2019 |
| WO | WO 2019/152857 | 8/2019 |
| WO | WO 2020/198485 | 10/2020 |

OTHER PUBLICATIONS

Torper et al. In vivo reprogramming of striatal NG2 glia into functional neurons that integrate into local host circuitry. Cell Reports 12:474-481, (Year: 2015).*

Addis et al., "Efficient conversion of astrocytes to functional midbrain dopaminergic neurons using a single polycistronic vector," PLoS One, Dec. 2011,6: e28719 (8 pages).

Aguirre and Gallo, "Postnatal neurogenesis and gliogenesis in the olfactory bulb from NG2-expressing progenitors of the subventricular zone," J Neurosci, Nov. 2004, 24: 10530-10541.

Aguirre et al., "NG2-expressing cells in the subventricular zone are type C-like cells and contribute to interneuron generation in the postnatal hippocampus," May 2004, J Cell Biol, 165: 575-589.

Anderson et al., "Interneuron migration from basal forebrain to neocortex: dependence on Dlx genes," Science, Oct. 1997, 278: 474-476.

Ascoli et al., "Petilla terminology: nomenclature of features of GABAergic interneurons of the cerebral cortex," Nat Rev Neurosci, Jul. 2008, 9: 557-568.

Atasoy et al., "A FLEX Switch Targets Channelrhodopsin-2 to Multiple Cell Types for Imaging and Long-Range Circuit Mapping," J. Neurosci., Jul. 2008, 28:7025-7030.

Bertrand et al., "Proneural genes and the specification of neural cell types," Nat. Rev. Neurosci., 2002, 3:517-530.

Boutin et al., "NeuroD1 induces terminal neuronal differentiation in olfactory neurogenesis," PNAS, Jan. 2010, 107: 1201-1206.

Brandao and Romcy-Pereira, "Interplay of environmental signals and progenitor diversity on fate specification of cortical GABAergic neurons," Front Cell Neurosci, Apr. 2015, 9: 149 (11 pages).

Brill et al, "A dlx2- and pax6-dependent transcriptional code for periglomerular neuron specification in the adult olfactory bulb," J Neurosci, Jun. 2008, 28: 6439-6452.

Buffo et al., "Origin and progeny of reactive gliosis: A source of multipotent cells in the injured brain," PNAS, Mar. 2008, 105:3581-3586.

Caiazzo et al., "Direct generation of functional dopaminergic neurons from mouse and human fibroblasts," Nature, 2011, 476: 224-227.

Chittajallu et al., "NG2-positive cells in the mouse white and grey matter display distinct physiological properties," J Physiol, Nov. 2004, 561: 109-122.

Cobos et al., "Mice lacking Dlx1 show subtype-specific loss of interneurons, reduced inhibition and epilepsy," Nat Neurosci, Aug. 2005, 8: 1059-1068.

Gangarossa et al., "Distribution and compartmental organization of GABAergic medium-sized spiny neurons in the mouse nucleus accumbens," Front Neural Circuits, Feb. 2013, 7:22 (20 pages).

GenBank Accession No. NM_002500, "*Homo sapiens* neuronal differentiation 1 (NEUROD1), transcript variant 1, mRNA," May 10, 2014, 4 pages.

GenBank Accession No. NM_004405, "*Homo sapiens* distal-less homeobox 2 (DLX2), mRNA," May 10, 2014, 5 pages.

GenBank Accession No. NP_002491, "neurogenic differentiation factor 1 [*Homo sapiens*]," May 10, 2014, 3 pages.

GenBank Accession No. NP_004396, "homeobox protein DLX-2 [*Homo sapiens*]," May 10, 2014, 3 pages.

Grande et al., "Environmental impact on direct neuronal reprogramming in vivo in the adult Brain," Nature Communications, 2013, 4: 2373.

Guo et al. "In vivo direct reprogramming of reactive glial cells into functional neurons after brain injury and in an Alzheimer's disease model," Cell Stem Cell, Feb. 2014, 14: 188-202.

He et al., "Multipotent stem cells from the mouse basal forebrain contribute GABAergic neurons and oligodendrocytes to the cerebral cortex during embryogenesis," J Neurosci, Nov. 2001, 21: 8854-8862.

Heinrich et al., "Directing Astroglia from the Cerebral Cortex into Subtype Specific Functional Neurons," PloS Biology, May 2010, 8: e1000373 (29 pages).

Heinrich et al., "Sox2-Mediated Conversion of NG2 Glia into Induced Neurons in the Injured Adult Cerebral Cortex," Stem Cell Reports, Dec. 2014, 3: 1000-1014.

Hill et al., "Modulation of oligodendrocyte generation during a critical temporal window after NG2 cell division," Nat Neurosci, Nov. 2014, 17: 1518-1527.

Howard et al., "Tropism and toxicity of adeno-associated viral vector serotypes 1,2,5,6,7,8,9 in rat neurons and glia in vitro," Virology, Mar. 2008, 372:24-34.

International Search Report and Written Opinion in International Application No. PCT/US2017/018398, dated May 8, 2017.

Kang et al., "NG2+ CNS Glial Progenitors Remain Committed to the Oligodendrocyte Lineage in Postnatal Life and following Neurodegeneration," Neuron, Nov. 2010, 68:668-681.

Karow et al., "Reprogramming of pericyte-derived cells of the adult human brain into induced neuronal cells," Cell Stem Cell, Oct. 2012, 11: 471-476.

Kawaguchi and Kondo, Parvalbumin, somatostatin and cholecystokinin as chemical markers for specific GABAergic interneuron types in the rat frontal cortexJ. Neurocytol., 2002, 31:277-287.

Kepecs and Fishell, "Interneuron Cell Types: Fit to form and formed to fit," Nature, Jan. 2014, 505:318-326.

Kuwabara et al., "Wnt-mediated activation of NeuroD1 and retroelements during adult neurogenesis," Nat. Neurosci., Sep. 2009, 12:1097-1105.

Liu et al., "Ascl 1 Converts Dorsal Midbrain Astrocytes into Functional Neurons In Vivo," J Neurosci, Jun. 2015, 35: 9336-9355.

Marin et al., "Origin and Molecular Specification of Striatal Interneurons," J. Neurosci., Aug. 2000, 20:6063-6076.

Markakis et al., "Comparative Transduction Efficiency of AAV Vector Serotypes 1-6 in the Substantia Nigra and Striatum of the Primate Brain," Mol. Ther., Mar. 2010, 18:588-593.

Marham et al., "Interneurons of the Neocortical Inhibitory System," Nat. Rev. Neurosci., Oct. 2004, 5:793-807.

Nicoleau et al., "Human Pluripotent Stem Cell Therapy for Huntington's Disease: Technical, Immunological, and Safety Challenges," Neurotherapeutics, 2011, 8: 562-576.

Nishiyama et al., "Polydendrocytes (NG2 cells): multifunctional cells with lineage plasticity," Nat. Rev. Neurosci., Jan. 2009, 10:9-22.

Niu et al., "In vivo reprogramming of astrocytes to neuroblasts in the adult brain," Nature Cell Biology, Oct. 2013, 15: 1164-1175.

Niu et al., "SOX2 reprograms resident astrocytes into neural progenitors in the adult brain," Stem Cell Reports, May 2015, 4: 780-794.

(56) References Cited

OTHER PUBLICATIONS

Pang et al., "Induction of human neuronal cells by defined transcription factors," Nature, 2011, 476: 220-223.
Panganiban and Rubenstein, "Developmental functions of the Distal-less/Dlx homeobox genes," Development, 2002, 129: 4371-4386.
Petryniak et al., "Dlx1 and Dlx2 control neuronal versus oligodendroglial cell fate acquisition in the developing forebrain," Neuron, Aug. 2007, 55: 417-433.
Ross and Tabrizi, "Huntington's disease: from molecular pathogenesis to clinical treatment," Lancet Neurol., Jan. 2011, 10:83-98.
Schnutgen et al., "A directional strategy for monitoring Cre-mediated recombination at the cellular level in the mouse," Nat. Biotechnol., Mar. 2003, 21:562-565.
Stuhmer et al., "Ectopic expression of the Dlx genes induces glutamic acid decarboxylase and Dlx expression," Development, 2002, 129: 245-252.
Su et al., "In vivo conversion of astrocytes to neurons in the injured adult spinal cord," Nature Communications, 2014, 5: 3338.
Takahashi and Yamanaka, "Induction of pluripotent stem cells from mouse embryonic and adult fibroblast cultures by defined factors," Cell, Aug. 2006, 126: 663-676.
Takahashi et al., "Induction of pluripotent stem cells from adult human fibroblasts by defined Factors," Cell, Nov. 2007, 131: 861-872.
Tamamaki et al., "Green fluorescent protein expression and colocalization with calretinin, parvalbumin, and somatostatin in the GAD67-GFP knock-in mouse," J Comp Neural, 2003, 467: 60-79.
Taniguchi, "Genetic dissection of GABAergic neural circuits in mouse neocortex," Front Cell Neurosci, Jan. 2014, 8: 8.
Torper et al., "In Vivo Reprogramming of Striatal NG2 Glia into Functional Neurons that Integrate into Local Host Circuitry," Cell Rep., Jul. 2015, 12(3):474-481.
Torper et al., "Generation of induced neurons via direct conversion in vivo," PNAS, 2013, 110: 7038-7043.
Tsai et al., "Regional astrocyte allocation regulates CNS synaptogenesis and repair," Science, Jul. 2012, 337: 358-362.
Tsoa et al., "Spatiotemporally different origins of NG2 progenitors produce cortical interneurons versus glia in the mammalian forebrain," PNAS, 2014, 111: 7444-7449.
Victor et al., "Generation of human striatal neurons by microRNA-dependent direct conversion of fibroblasts," Neuron, Oct. 2014, 84: 311-323.
Vielbuchen et al., "Direct conversion of fibroblasts to functional neurons by defined Factors," Nature, Feb. 2010, 463:1035-1041.
Walker, "Huntington's disease," Lancet, 2007, 369:218-228.
Wang et al., "Dlx5 and Dlx6 regulate the development of parvalbumin-expressing cortical interneurons." J Neurosci, Apr. 2010, 30: 5334-5345.
Wonders and Anderson, "The origin and specification of cortical interneurons," Nat Rev Neurosci, Sep. 2006, 7: 687-696.
Yoo et al., "MicroRNA-mediated conversion of human fibroblasts to neurons," Nature, 2011, 476: 228-231.
Yung et al., "Differential modulation of BMP signaling promotes the elaboration of cerebral cortical GABAergic neurons or oligodendrocytes from a common sonic hedgehog-responsive ventral forebrain progenitor species," PNAS, Dec. 2002, 99: 16273-16278.
Zhang and Barres, "Astrocyte heterogeneity: an underappreciated topic in neurobiology," Curr Opin Neurobiol, Oct. 2010, 20: 588-594.
Zhang et al., "Small Molecules Efficiently Reprogram Human Astroglial Cells into Functional Neurons," Cell Stem Cell., Oct. 2015, 17(6):735-747.
Zhao et al., "Distinct Morphological Stages of Dentate Granule Neuron Maturation in the Adult Mouse Hippocampus," J. Neurosci., Jan. 2006, 26: 3-11.
Zhong et al., "The Wnt receptor Ryk controls specification of GABAergic neurons versus oligodendrocytes during telencephalon development," Development, 2011, 138: 409-419.
Extended European Search Report in European App.No. 17753935.0 dated Jan. 18, 2019, 277 pages.
Grande et al., "Environmental impact on direct neuronal reprogramming in vivo in the adult brain," Nature communications, 4(1):1-2, Aug. 2013.
Wu et al., "Gene therapy conversion of striatal astrocytes into GABAergic neurons in mouse models of Huntington's disease," Nature communications, 11(1):1-8, Feb. 2020.
Yamashita et al., "In vivo direct reprogramming of glial linage to mature neurons after cerebral ischemia," Sci Rep., 9(1):10956, Jul. 2019.
Abraira and Ginty, "The sensory neurons of touch," Neuron, Aug. 2013, 79(4):618-39.
Adams and Hicks, "Spasticity after spinal cord injury," Spinal cord, Oct. 2005, 43(10):577-86.
Adil et al., "hPSC-derived striatal cells generated using a scalable 3D hydrogel promote recovery in a Huntington disease mouse model," Stem cell reports, May 2018, 10(5):1481-91.
Altschul et al., "Basic local alignment search tool," Journal of molecular biology, Oct. 1990, 215(3):403-10.
Altschul et al., "Gapped BLAST and PSI-BLAST: a new generation of protein database search programs," Nucleic acids research, Sep. 1997, 25(17):338-9402.
Anderson et al., "Astrocyte scar formation aids central nervous system axon regeneration," Nature, Apr. 2016, 532(7598):195-200.
Anderson et al., "Differential origins of neocortical projection and local circuit neurons: role of D1x genes in neocortical interneuronogenesis," Cerebral Cortex, Sep. 1999, 9(6):646-54.
animalresearch.info [online] "Huntington's disease," Nov. 5, 2014, [retrieved on Oct. 21, 2020], Retrieved from: URL<http://www.animalresearch.info/en/medical-advances/diseases-research/huntingtons-disease/> 5 pages.
Baird et al., "The staircase test of skilled reaching in mice," Brain research bulletin, Jan. 2001, 54(2):243-50.
Bani-Yaghoub et al., "Role of Sox2 in the development of the mouse neocortex," Developmental biology, Jul. 2006, 295(1):52-66.
Barker et al., "New approaches for brain repair—from rescue to reprogramming," Nature, May 2018, 557(7705):329-34.
Barry et al., "Striatal direct and indirect pathway output structures are differentially altered in mouse models of Huntington's disease," Journal of Neuroscience, May 2018, 38(20):4678-94.
Baskin et al., "Two effective behavioral tasks for evaluating sensorimotor dysfunction following traumatic brain injury in mice," Journal of neuroscience methods, Oct. 2003, 129(1):87-93.
Bates et al., "Huntington disease," Nat. Rev. Dis. Primers, Apr. 2015, 1(1):15005.
Bayer and Wirths, "Intracellular accumulation of amyloid-Beta-a predictor for synaptic dysfunction and neuron loss in Alzheimer's disease," Frontiers in aging neuroscience, Mar. 2010, 2:8.
Bermingham et al., "Proprioceptor pathway development is dependent on Math 1," Neuron, May 2001, 30(2):411-22.
Bonnard et al., "Recent advances in nanomedicine for ischemic and hemorrhagic stroke," Stroke, May 2019, 50(5):1318-24.
Brennan et al., "Molecular pathology of tumors," Cell, Oct. 2013, 155(2):462-77.
Brulet et al., "NEUROD1 instructs neuronal conversion in non-reactive astrocytes," Stem cell reports, Jun. 2017, 8(6):1506-15.
Burda and Sofroniew, "Reactive gliosis and the multicellular response to CNS damage and disease," Neuron, Jan. 2014, 81(2):229-48.
Busch et al., "Alzheimer's disease and retinal neurodegeneration share a consistent stress response of the neurovascular unit," Cellular physiology and biochemistry, 2012, 30(6):1436-43.
Bylund et al., "Vertebrate neurogenesis is counteracted by Sox1-3 activity," Nature neuroscience, Nov. 2003, 6(11):1162-8.
Cancer Genome Atlas Research Network, "Comprehensive genomic characterization defines human glioblastoma genes and core pathways," Nature, Oct. 2008, 455(7216):1061.
Castillo et al., "Comparative profiling of cortical gene expression in Alzheimer's disease patients and mouse models demonstrates a link between amyloidosis and neuroinflammation," Scientific reports, Dec. 2017, 7(1):1-6.
Celis et al., "High-resolution two-dimensional gel electrophoresis of proteins: isoelectric focusing and nonequilibrium pH gradient electrophoresis (NEPHGE)," InCell Biology, Jan. 1994, (pp. 222-230), Academic Press.

(56) References Cited

OTHER PUBLICATIONS

Chan et al., "Engineered AAVs for efficient noninvasive gene delivery to the central and peripheral nervous systems," Nature neuroscience, Aug. 2017, 20(8):1172-9.
Chen et al., "A NeuroD1 AAV-based gene therapy for functional brain repair after ischemic injury through in vivo astrocyte-to-neuron conversion," Molecular Therapy, Jan. 2020, 28(1):217-34.
Chen et al., "GAD67-GFP knock-in mice have normal sleep-wake patterns and sleep homeostasis," Neuroreport, Feb. 2010, 21(3):216.
Chen et al., "The basic helix-loop-helix transcription factor olig2 is critical for reactive astrocyte proliferation after cortical injury," Journal of Neuroscience, Oct. 2008, 28(43):10983-9.
Cheng et al., "Lbxl and T1x3 are opposing switches in determining GABAergic versus glutamatergic transmitter phenotypes," Nature neuroscience, Nov. 2005, 8(11):1510-5.
Cho and Tsai, "The role of BETA2/NeuroD1 in the development of the nervous system," Molecular neurobiology, Aug. 2004, 30(1):35-47.
Cho et al., "Targeted genome engineering in human cells with the Cas9 RNA-guided endonuclease," Nat Biotechnol, Mar. 2013, 31(3):230-2.
Choi et al., "Hippocampus-based contextual memory alters the morphological characteristics of astrocytes in the dentate gyrus," Molecular brain, Dec. 2016, 9(1):72.
Claassen et al., "Tetrabenazine treatment patterns and outcomes for chorea associated with Huntington disease: a retrospective chart review," Journal of Huntington's Disease, Jan. 2018, 7(4):345-53.
Clarkson et al., "Reducing excessive GABA-mediated tonic inhibition promotes functional recovery after stroke," Nature, Nov. 2010, 468(7321):305-9.
Cong et al., "Multiplex genome engineering using CRISPR/Cas systems," Science, Feb. 2013, 339(6121):819-23.
Cregg et al., "Functional regeneration beyond the glial scar," Experimental neurology, Mar. 2014, 253:197-207.
Crooke, "Ionis: the Leader in RNA-Targeted," [dated Oct. 21, 2020], Retrieved from: <Therapeuticshttps://ir.ionispharma.com/static-files/e034473b-e000-4b84-88a6-0dfOc5b6a79e>, 94 pages.
Deng et al., "Sequential postsynaptic maturation governs the temporal order of GABAergic and glutamatergic synaptogenesis in rat embryonic cultures," J. Neurosci., Oct. 2007, 27(40):10860-10869.
di Val Cervo et al., "Induction of functional dopamine neurons from human astrocytes in vitro and mouse astrocytes in a Parkinson's disease model," Nature biotechnology, May 2017, 35(5):444-52.
DiCarlo et al., "Genome engineering in Saccharomyces cerevisiae using CRISPR-Cas systems," Nucleic. Acids Res., Apr. 2013, 41(7):4336-43.
Dittgen et al., "Lentivirus-based genetic manipulations of cortical neurons and their optical and electrophysiological monitoring in vivo," Proceedings of the National Academy of Sciences, Dec. 2004, 101(52):18206-11.
El-Serag, "Epidemiology of viral hepatitis and hepatocellular carcinoma," Gastroenterology, May 2012, 142(6):1264-73.
Escartin and Bonvento, "Targeted activation of astrocytes: a potential neuroprotective strategy," Molecular neurobiology, Dec. 2008, 38(3):231-41.
Ferreira et al., "From the periphery to the brain: Lipocalin-2, a friend or foe?" Progress in neurobiology, Aug. 2015, 131:120-36.
Filous and Schwab, "Determinants of axon growth, plasticity, and regeneration in the context of spinal cord injury," The American journal of pathology, Jan. 2018, 188(1):53-62.
Foust et al., "Intravascular AAV9 preferentially targets neonatal neurons and adult astrocytes," Nature biotechnology, Jan. 2009, 27(1):59-65.
Freeman, "Specification and morphogenesis of astrocytes," Science, Nov. 2010, 330(6005):774-8.
Frost and Li, "The role of astrocytes in amyloid production and Alzheimer's disease," Open biology, Dec. 2017, 7(12):170228.
Fu et al., "MiR-30a-5p ameliorates spinal cord injury-induced inflammatory responses and oxidative stress by targeting Neurod 1 through MAPK/ERK signalling. Clinical and Experimental Pharmacology and Physiology," Jan. 2018, 45(1):68-74.
Fuxe et al., "Endothelin-1 induced lesions of the frontoparietal cortex of the rat. A possible model of focal cortical ischemia," Neuroreport, Jul. 1997, 8(11):2623-9.
Gallo and Deneen, "Glial development: the crossroads of regeneration and repair in the CNS" Neuron, Jul. 2014, 83(2):283-308.
Games et al., "Alzheimer-type neuropathology in transgenic mice overexpressing V717F (β-amyloid precursor protein," Nature, Feb. 1995, 373(6514):523-7.
Gao et al., "Neurod1 is essential for the survival and maturation of adult-born neurons," Nature neuroscience, Sep. 2009, 12(9):1090-2.
Gascón et al., "Identification and successful negotiation of a metabolic checkpoint in direct neuronal reprogramming," Cell stem cell, Mar. 2016, 18(3):396-409.
GenBank Accession No. AAB32188.1, "Nrf2 [Homo sapiens]," dated Mar. 3, 1995, 2 pages.
GenBank Accession No. AAH06221.2, "NK2 homeobox 1 [Homo sapiens]," dated Jan. 30, 2008, 2 pages.
GenBank Accession No. AAH06545.2, "FOXA2 protein, partial [Homo sapiens]," dated Oct. 8, 2003, 2 pages.
GenBank Accession No. AAH11780.1, "Forkhead box A2 [Homo sapiens],", dated Jul. 15, 2006, 2 pages.
GenBank Accession No. AAH33890.1, "Forkhead box A1 [*Homo sapiens*]," dated Jul. 17, 2006, 2 pages.
GenBank Accession No. AAH36847.1, "Neurogenin 2 [*Homo sapiens*]," dated Jul. 15, 2006, 2 pages.
GenBank Accession No. AAH46460.1, "Forkhead box J1 [*Homo sapiens*]," dated Jul. 15, 2006, 2 pages.
GenBank Accession No. AAH53850.1, "Forkhead box Q1 [*Homo sapiens*]," dated Jul. 15, 2006, 2 pages.
GenBank Accession No. AAH64698.1, "Transcription factor CP2-like 1 [*Homo sapiens*]," dated Jul. 17, 2006, 2 pages.
GenBank Accession No. AAH80524.1, "E4F transcription factor 1 [*Homo sapiens*]," dated Jul. 15, 2006, 3 pages.
GenBank Accession No. AAH80868.1, "Nkx2-1 protein [Mus musculus]," dated Oct. 1, 2007, 2 pages.
GenBank Accession No. AAH89442.1, "Forkhead box F1 [*Homo sapiens*]," dated Jan. 30, 2008, 2 pages.
GenBank Accession No. AAI43480.1, "GATA4 protein [*Homo sapiens*], "GATA4 protein [Homo sapiens], dated Jan. 8, 2009, 2 pages.
GenBank Accession No. ACA06111.1, "forkhead box A2 [*Homo sapiens*]" dated Feb. 20, 2008, 1 page.
GenBank Accession No. EAW51092.1, "forkhead box N1 [*Homo sapiens*]," dated Mar. 23, 2015, 2 pages.
GenBank Accession No. EAW55070.1, "forkhead box Q1 [*Homo sapiens*]," dated Mar. 23, 2015, 2 pages.
GenBank Accession No. EAW65844.1, "forkhead box A1 [*Homo sapiens*]," dated Mar. 23, 2015, 2 pages.
GenBank Accession No. EAW95250.1, "transcription factor CP2-like 1, isoform Cra _A [*Homo sapiens*]," dated Mar. 23, 2015, 2 pages.
GenBank Accession No. EAW95251.1, "transcription factor CP2-like 1, isoform CRA _b [*Homo sapiens*]," dated Mar. 23, 2015, 2 pages.
GenBank Accession No. EAW95424.1, "forkhead box F1 [*Homo sapiens*]," dated Mar. 23, 2015, 2 pages.
GenBank Accession No. EAX06278.1, "neurogenin 2 [*Homo sapiens*]," dated Mar. 23, 2015, 2 pages.
GenBank Accession No. NM_001308093.1, "Homo sapiens GATA binding protein 4 (GATA4), transcript variant 1, Mrna," dated Apr. 28, 2015, 4 pages.
GenBank Accession No. NM_002500.4 "Homo sapiens neuronal differentiation 1 (NEUROD1), Mrna," dated May 10, 2014, 4 pages.
GenBank Accession No. NM_004316.3, "Homo sapiens achaete-scute family bHLH transcription factor 1 (ASCL1), mRNA," dated May 3, 2014, 4 pages.
GenBank Accession No. NM_021784.4, "Homo sapiens forkhead box A2 (FOXA2), transcript variant 1, mRNA" dated Feb. 2, 2014, 4 pages.
GenBank Accession No. NM_024019.3,"Homo sapiens neurogenin 2 (NEUROG2), mRNA," dated Mar. 16, 2014, 3 pages.

(56) References Cited

OTHER PUBLICATIONS

GenBank Accession No. NM_178849.2, "Homo sapiens hepatocyte nuclear factor 4, alpha (HNF4A), transcript variant 1, Mrna," Oct. 15, 2014, 4 pages.
GenBank Accession No. NP_000448.3, "hepatocyte nuclear factor 4-alpha isoform HNF4alpha2 [Homo sapiens]" dated Oct. 15, 2014, 3 pages.
GenBank Accession No. NP_000449.1, "hepatocyte nuclear factor 1-beta isoform 1 [Homo sapiens]," dated Jan. 16, 2015, 3 pages.
GenBank Accession No. NP_001025174.1, "hepatocyte nuclear factor 4-alpha isoform HNF4alpha7 [Homo sapiens]" dated Oct. 15, 2014, 3 pages.
GenBank Accession No. NP_001025175.1, "hepatocyte nuclear factor 4-alpha isoform HNF4alpha9 [Homo sapiens]," dated Oct. 15, 2014, 3 pages.
GenBank Accession No. NP_001073136.1, "homeobox protein Nkx-2.1 isoform 1 [Homo sapiens]," dated May 10, 2014, 3 pages.
GenBank Accession No. NP_001108450.1, "tumor protein 63 isoform 2 [Homo sapiens]," dated May 4, 2014, 3 pages.
GenBank Accession No. NP_001108451.1, "tumor protein 63 isoform 3 [Homo sapiens]," dated May 4, 2014, 3 pages.
GenBank Accession No. NP_001159395.1, "hepatocyte nuclear factor 1-beta isoform 2 [Homo sapiens]," dated May 11, 2014, 3 pages.
GenBank Accession No. NP_001230009.1, "ETS-related transcription factor Elf-5 isoform 3 [Homo sapiens]," dated Feb. 26, 2014, 3 pages.
GenBank Accession No. NP_001230010.1, "ETS-related transcription factor Elf-5 isoform 4 [Homo sapiens]," dated Aug. 9, 2014, 3 pages.
GenBank Accession No. NP_001245284.1, "hepatocyte nuclear factor 4-alpha isoform HNF4alpha4 [Homo sapiens]," dated Oct. 15, 2014, 3 pages.
GenBank Accession No. NP_001274111.1, "hepatocyte nuclear factor 4-alpha isoform HNF4alpha10 [*Homo sapiens*]," dated Oct. 15, 2014, 3 pages.
GenBank Accession No. NP_001274112.1, "hepatocyte nuclear factor 4-alpha isoform HNF4alpha11 [*Homo sapiens*]," dated Oct. 15, 2014, 3 pages.
GenBank Accession No. NP_001274113.1, "hepatocyte nuclear factor 4-alpha isoform HNF4alpha12 [*Homo sapiens*]," dated Jan. 18, 2014, 3 pages.
GenBank Accession No. NP_001291215.1, "hepatocyte nuclear factor 1-beta isoform 3 [*Homo sapiens*]," dated Jan. 15, 2015, 3 pages.
GenBank Accession No. NP_001295022.1, "transcription factor GATA-4 isoform 1 [*Homo sapiens*]," dated Apr. 28, 2015, 3 pages.
GenBank Accession No. NP_001295023.1, "transcription factor GATA-4 isoform 3 [*Homo sapiens*]," dated Apr. 28, 2015, 3 pages.
GenBank Accession No. NP_001316073.1, "tumor protein 63 isoform 7 [*Homo sapiens*]," dated Jul. 2, 2016, 3 pages.
GenBank Accession No. NP_001316893.1, "tumor protein 63 isoform 13 [*Homo sapiens*]," dated Aug. 13, 2016, 3 pages.
GenBank Accession No. NP_001350793.1, "B-cell lymphoma/leukemia 11A isoform 4 [*Homo sapiens*]," dated Jun. 3, 2018, 3 pages.
GenBank Accession No. NP_001352538.1, "B-cell lymphoma/leukemia 11A isoform 5 [*Homo sapiens*]," dated Sep. 12, 2018, 3 pages.
GenBank Accession No. NP_001356298.1, "forkhead box protein N1 [*Homo sapiens*]," dated Apr. 8, 2019, 3 pages.
GenBank Accession No. NP_001361203.1, "transcription factor GATA-4 isoform 4 [*Homo sapiens*]," dated Sep. 18, 2019, 3 pages.
GenBank Accession No. NP_001413.1, "ETS-related transcription factor Elf-5 isoform 2 [*Homo sapiens*]," dated May 3, 2014, 3 pages.
GenBank Accession No. NP_001442.2, "forkhead box protein F1 [*Homo sapiens*]," dated May 11, 2014, 3 pages.
GenBank Accession No. NP_001445.2, "forkhead box protein J1 [*Homo sapiens*]," dated May 3, 2014, 3 pages.
GenBank Accession No. NP_002043.2, "transcription factor GATA-4 [*Homo sapiens*]," dated Sep. 23, 2014, 3 pages.
GenBank Accession No. NP_002193.2, "insulin gene enhancer protein ISL-1 [*Homo sapiens*]," dated Aug. 26, 2018, 3 pages.
GenBank Accession No. NP_002491.2, "neurogenic differentiation factor 1 [*Homo sapiens*]," dated May 10, 2014, 3 pages.
GenBank Accession No. NP_003308.1, "homeobox protein Nkx-2.1 isoform 2 [*Homo sapiens*]"dated Apr. 19, 2014, 3 pages.
GenBank Accession No. NP_003584.2, "forkhead box protein N1 [*Homo sapiens*]," dated May 3, 2014, 3 pages.
GenBank Accession No. NP_003713.3, "tumor protein 63 isoform 1 [*Homo sapiens*]," dated May 4, 2014, 3 pages.
GenBank Accession No. NP_004307.2, "achaete-scute homolog 1 [*Homo sapiens*]," dated May 3, 2014, 2 pages.
GenBank Accession No. NP_004487.2, "hepatocyte nuclear factor 3-alpha [*Homo sapiens*]," dated May 11, 2014, 3 pages.
GenBank Accession No. NP_055368.1, "transcription factor CP2-like protein 1 [*Homo sapiens*]," dated May 14, 2014, 3 pages.
GenBank Accession No. NP_068556.2, "hepatocyte nuclear factor 3-beta isoform 1 [*Homo sapiens*]," dated Feb. 2, 2014, 3 pages.
GenBank Accession No. NP_075044.2, "B-cell lymphoma/leukemia 11A isoform 1 [*Homo sapiens*]," dated May 24, 2014, 4 pages.
GenBank Accession No. NP_076924.1, "neurogenin-2 [*Homo sapiens*]," dated Mar. 16, 2014, 3 pages.
GenBank Accession No. NP_150285.3, "forkhead box protein Q1 [*Homo sapiens*]," dated May 10, 2014, 3 pages.
GenBank Accession No. NP_710141.1, "hepatocyte nuclear factor 3-beta isoform 2 [*Homo sapiens*]" dated Feb. 2, 2014, 3 pages.
GenBank Accession No. NP_787110.2, "hepatocyte nuclear factor 4-alpha isoform HNF4alpha8 [*Homo sapiens*]," dated Oct. 15, 2014, 3 pages.
GenBank Accession No. NP_849180.1, "hepatocyte nuclear factor 4-alpha isoform HNF4alpha1 [*Homo sapiens*]," Oct. 15, 2014, 3 pages.
GenBank Accession No. NP_849181.1, "hepatocyte nuclear factor 4-alpha isoform HNF4alpha3 [*Homo sapiens*]," dated Oct. 15, 2014, 3 pages.
GenBank Accession No. NP_938195.1, "ETS-related transcription factor Elf-5 isoform 1 [*Homo sapiens*]," dated Jan. 26, 2014, 3 pages.
GenBank Accession No. P27889.2, "RecName: Full=Hepatocyte nuclear factor 1-beta; Short=HNF-1-beta; Short=HNF-1B; AltName: Full=Homeoprotein LFB3; AltName: Full=Transcription factor 2; Short=TCF-2," dated Feb. 4, 2015, 4 pages.
GenBank Accession No. P35680.1, "RecName: Full=Hepatocyte nuclear factor 1-beta; Short=HNF-1-beta; Short=HNF-1B; AltName: Full=Homeoprotein LFB3; AltName: Full=Transcription factor 2; Short=TCF-2; AltName: Full=Variant hepatic nuclear factor 1; Short=vHNF1," dated Jan. 7, 2015, 9 pages.
GenBank Accession No. Q12946.2, "RecName: Full=Forkhead box protein F1; AltName: Full=Forkhead-related activator 1; Short=FREAC-1; AltName: Full=Forkhead-related protein FKHL5; AltName: Full=Forkhead-related transcription factor 1," dated Feb. 4, 2015, 6 pages.
GenBank Accession No. Q13562.3, "RecName: Full=Neurogenic differentiation factor 1; Short=NeuroD; Short=NeuroD1; AltName: Full=Class A basic helix-loop-helix protein 3; Short=bHLHa3," dated Feb. 4, 2015, 6 pages.
GenBank Accession No. Q66K89.2, RecName: Full=Transcription factor E4F1; AltName: Full=E4F transcription factor 1; AltName: Full=Putative E3 ubiquitin-protein ligase E4F1; AltName: Full=Transcription factor E4F; AltName: Full=p120E4F; AltName: Full=p50E4F, dated Feb. 4, 2015, 9 pages.
GenBank Accession No. Q9H165.2, "RecName: Full=B-cell lymphoma/leukemia 11A; Short=BCL-11A; AltName: Full=B-cell CLL/lymphoma 11A; AltName: Full=COUP-TF-interacting protein 1; AltName: Full=Ecotropic viral integration site 9 protein homolog; Short=Evi-9; AltName: Full=Zinc finger protein 856," dated Feb. 4, 2015, 7 pages.
GenBank Accession No. Q9Y261.1, "RecName: Full=Hepatocyte nuclear factor 3-beta; Short=HNF-3-beta; Short=HNF-3B; AltName:

(56) References Cited

OTHER PUBLICATIONS

Full=Forkhead box protein A2; AltName: Full=Transcription factor 3B; Short=TCF-3B," dated Feb. 4, 2015, 5 pages.
GenBank Accession No. XP_005260464.1, "Predicted: hepatocyte nuclear factor 4-alpha isoform X1 [*Homo sapiens*]," Feb. 3, 2014, 2 pages.
GenBank Accession NP_001350675.1, "LIM/homeobox protein Lhx3 isoform c [*Homo sapiens*]," dated May 30, 2018, 3 pages.
Gentet, "Functional diversity of supragranular GABAergic neurons in the barrel cortex," Frontiers in neural circuits, Aug. 2012, 6:52.
Ginhoux et al., " Fate mapping analysis reveals that adult microglia derive from primitive macrophages," Science, Nov. 2010, 330(6005):841-5.
Goldman, "Stem and progenitor cell-based therapy of the central nervous system: hopes, hype, and wishful thinking," Cell stem cell, Feb. 2016, 18(2):174-88.
Gómez-Isla et al., "Profound loss of layer II entorhinal cortex neurons occurs in very mild Alzheimer's disease," Journal of Neuroscience, Jul. 1996, 16(14):4491500.
González-Reyes et al., "Involvement of astrocytes in Alzheimer's disease from a neuroinflammatory and oxidative stress perspective," Frontiers in Molecular Neuroscience, Dec. 2017, 10:427.
Graham et al., "SOX2 functions to maintain neural progenitor identity," Neuron, Aug. 2003, 39(5):749-65.
Gross et al., "Lbx1 specifies somatosensory association interneurons in the dorsal spinal cord," Neuron, May 2002, 34(4):535-49.
Gu et al., "R gene expression induced by a type-III effector triggers disease resistance in rice," Nature, Jun. 2005, 435(7045):1122-5.
Guichet et al., "Cell death and neuronal differentiation of glioblastoma stem-like cells induced by neurogenic transcription factors," Glia, Feb. 2013, 61(2):225-39.
Halees et al., "PromoSer: a large-scale mammalian promoter and transcription start site identification service," Nucleic acids research, Jul. 2003, 31(13):3554-9.
He and Jin, "Intrinsic control of axon regeneration," Neuron, May 2016, 90(3):437-51.
He et al., "The regulation of microRNA expression by DNA methylation in hepatocellular carcinoma," Molecular bioSystems, Feb. 2015, 11(2):532-9.
Heppner et al., "Immune attack: the role of inflammation in Alzheimer disease," Nature Reviews Neuroscience, Jun. 2015, 16(6):358-72.
Herdewijn P, editor. Oligonucleotide synthesis: methods and applications. Springer Science & Business Media; 2005.
Herrmann et al., "STAT3 is a critical regulator of astrogliosis and scar formation after spinal cord injury," Journal of Neuroscience, Jul. 2008, 28(28):7231-43.
High and Roncarolo, "Gene Therapy," N. Engl. J. Med., Aug. 2019, 381(5):455-464.
Holley et al., "Therapeutic effects of stem cells in rodent models of Huntington's disease: Review and electrophysiological findings," CNS Neuroscience & Therapeutics, Apr. 2018, 24(4):329-42.
Hong et al., "Complement and microglia mediate early synapse loss in Alzheimer mouse models," Science, May 2016, 352(6286):712-6.
Hong et al., "Functional requirement of dicerl and miR-17-5p in reactive astrocyte proliferation after spinal cord injury in the mouse," Glia, Dec. 2014, 62(12):2044-60.
Hongbo, "The Molecular Mechanism of the NeuroD1 Gene Regulation Induced by All-trans Retinoic Acid in Neural Cells Differentiation," China Doctor Dissertation Full-text, Database (Electronic Journal) Basic Science Volume, Nov. 2011, 11:A006-4 (English abstract).
Horie et al., "Mouse model of focal cerebral ischemia using endothelin-1," Journal of neuroscience methods, Aug. 2008, 173(2):286-90.
Huang and Mucke, "Alzheimer mechanisms and therapeutic strategies," Cell, Mar. 2012, 148(6):1204-22.
Huang et al., "Ptf1a, Lbxl and Pax2 coordinate glycinergic and peptidergic transmitter phenotypes in dorsal spinal inhibitory neurons," Developmental biology, Oct. 2008, 322(2):394-405.
Hughes et al., "Focal lesions in the rat central nervous system induced by endothelin-1," Journal of Neuropathology & Experimental Neurology, Dec. 2003, 62(12):1276-86.
Hwang et al., "Efficient genome editing in zebrafish using a CRISPR-Cas system," Nat. Biotechnol., Mar. 2013, 31(3):227-9.
Jaunmuktane et al., "Evidence for human transmission of amyloid-β pathology and cerebral amyloid angiopathy," Nature, Sep. 2015, 525(7568):247-50.
Jiang et al., "Motor and behavioral phenotype in conditional mutants with targeted ablation of cortical D1 dopamine receptor-expressing cells," Neurobiology of disease, Apr. 2015, 76:137-58.
Jiang et al., "RNA-guided editing of bacterial genomes using CRISPR-Cas systems," Nature biotechnology, Mar. 2013, 31(3):233-9.
Jinek et al., "A programmable dual-RNA—guided Dna endonuclease in adaptive bacterial immunity," Science, Aug. 2012, 337(6096):816-21.
Karlin and Altschul, "Applications and statistics for multiple high-scoring segments in molecular sequences," Proceedings of the National Academy of Sciences, Jun. 1993, 90(12):5873-7.
Karlin and Altschul, "Methods for assessing the statistical significance of molecular sequence features by using general scoring schemes," Proceedings of the National Academy of Sciences, Mar. 1990, 87(6):2264-8.
Kay et al., "A bacterial effector acts as a plant transcription factor and induces a cell size regulator," Science, Oct. 2007, 318(5850):648-51.
Kim et al., "Hybrid restriction enzymes: zinc finger fusions to Fok I cleavage domain," Proc Natl Acad Sci USA, Feb. 1996, 93(3):1156-60.
Kimbrough et al., "Vascular amyloidosis impairs the gliovascular unit in a mouse model of Alzheimer's disease," Brain, Dec. 2015, 138(12):3716-33.
Kitagawa, "Therapeutic application of cell transplantation and increased neurogenesis in cerebral infarction," Rinsho shinkeigaku= Clinical neurology, Nov. 2004, 44(11):756.
Koprivica et al., "EGFR activation mediates inhibition of axon regeneration by myelin and chondroitin sulfate proteoglycans," Science, Oct. 2005, 310(5745): 106-10.
Kordasiewicz et al., "Sustained therapeutic reversal of Huntington's disease by transient repression of huntingtin synthesis," Neuron, Jun. 2012, 74(6):1031-44.
Kreitzer, "Physiology and pharmacology of striatal neurons," Annual review of neuroscience, Jul. 2009, 32:127-47.
Kunz et al., "Reduced grid-cell—like representations in adults at genetic risk for Alzheimer's disease," Science, Oct. 2015, 350(6259):430-3.
LaFerla et al., "Intracellular amyloid-β in Alzheimer's disease," Nature Reviews Neuroscience, Jul. 2007, 8(7):499-509.
Lambert et al., "Targeting transcription factors for cancer treatment," Molecules, Jun. 2018, 23(6):1479.
Lee et al., "Conversion of Xenopus ectoderm into neurons by NeuroD, a basic helix-loop-helix protein," Science, May 1995, 268(5212):836-44.
Lei et al., "Non-engineered and engineered adult neurogenesis in mammalian brains," Frontiers in neuroscience, Feb. 2019, 13:131.
Li and Chen, "In vivo reprogramming for CNS repair: regenerating neurons from endogenous glial cells," Neuron, Aug. 2016, 91(4):728-38.
Liddelow and Barres, "Reactive astrocytes: production, function, and therapeutic potential," Immunity, Jun. 2017, 46(6):957-67.
Liddelow et al., "Neurotoxic reactive astrocytes are induced by activated microglia," Nature, Jan. 2017, 541(7638):481-7.
Limon et al., "Loss of functional GABAA receptors in the Alzheimer diseased brain," Proceedings of the National Academy of Sciences, Jun. 2012, 109(25):10071-6.
Liu et al., "Differential neuronal reprogramming induced by NeuroD1 from astrocytes in grey matter versus white matter," Neural regeneration research, Feb. 2020, 15(2):342.
Lu et al., "Molecular and cellular development of spinal cord locomotor circuitry," Frontiers in molecular neuroscience, Jun. 2015, 8:25.

(56) References Cited

OTHER PUBLICATIONS

Lu et al., "Prolonged human neural stem cell maturation supports recovery in injured rodent CNS," The Journal of clinical investigation, Sep. 2017, 127(9):3287-99.
Lu et al., "Turning reactive glia into functional neurons in the brain. Cell Stem Cell," Cell Stem Cell, 14:133-34, Feb. 2014.
Ma et al., "Distinct subtypes of somatostatin-containing neocortical interneurons revealed in transgenic mice," Journal of Neuroscience, May 2006, 26(19):5069-82.
Ma et al., "Human embryonic stem cell-derived GABA neurons correct locomotion deficits in quinolinic acid-lesioned mice," Cell stem cell, Apr. 2012, 10(4):455-64.
MacDonald et al., "A novel gene containing a trinucleotide repeat that is expanded and unstable on Huntington's disease chromosomes," Cell, Mar. 1993, 26;72(6):971-83.
Makarova et al., "Evolution and classification of the CRISPR—Cas systems," Nature Reviews Microbiology, Jun. 2011, 9(6):467-77.
Mali et al., "RNA-guided human genome engineering via Cas9," Science, Feb. 2013, 339(6121):823-6.
Mangiarini et al., "Exon 1 of the HD gene with an expanded CAG repeat is sufficient to cause a progressive neurological phenotype in transgenic mice," Cell, Nov. 1996, 87(3):493-506.
Marchesi, "Alzheimer's dementia begins as a disease of small blood vessels, damaged by oxidative-induced inflammation and dysregulated amyloid metabolism: implications for early detection and therapy," The FASEB Journal, Jan. 2011, 25(1):5-13.
Matsuda et al., "Pioneer factor NeuroD1 rearranges transcriptional and epigenetic profiles to execute microglia-neuron conversion," Neuron, Feb. 2019, 101(3):472-85.
McKinsey et al., "Dlx1&2-dependent expression of Zfhx1b (Sip1, Zeb2) regulates the fate switch between cortical and striatal interneurons," Neuron, Jan. 2013, 77(1):83-98.
Medeiros and LaFerla, "Astrocytes: conductors of the Alzheimer disease neuroinflammatory symphony," Experimental neurology, Jan. 2013, 239:133-8.
Menalled et al., "Systematic behavioral evaluation of Huntington's disease transgenic and knock-in mouse models," Neurobiol. Dis., Sep. 2009, 35(3):319-36.
Miao et al., "Up-regulation of GBP2 is associated with neuronal apoptosis in rat brain cortex following traumatic brain injury," Neurochemical research, May 2017, 42(5):1515-23.
Miniarikova et al., "AAVS-miHTT gene therapy demonstrates suppression of mutant huntingtin aggregation and neuronal dysfunction in a rat model of Huntington's disease," Gene therapy, Oct. 2017, 24(10):630-9.
Mitew et al., "Altered synapses and gliotransmission in Alzheimer's disease and AD model mice," Neurobiology of aging, Oct. 2013, 34(10):2341-51.
Miyata et al., "NeuroD is required for differentiation of the granule cells in the cerebellum and hippocampus," Genes & development, Jul. 1999, 13(13):1647-52.
Moghimi et al., "Nanomedicine: current status and future prospects," The FASEB journal, Mar. 2005, 19(3):311-30.
Morgan, "Gene therapy protocols," Springer Science & Business Media, 2002, 69:1-30.
Morrow et al., "NeuroD regulates multiple functions in the developing neural retina in rodent," Development, Jan. 1999, 126(1):23-36.
Myers and Miller, "Optimal alignments in linear space," Bioinformatics, Mar. 1988, 4(1):11-7.
Norenberg et al., "The pathology of human spinal cord injury: defining the problems," J. Neurotrauma, 2004, 21:429-440.
Nussbaum et al., "Prion-like behaviour and tau-dependent cytotoxicity of pyroglutamylated amyloid-β," Nature, May 2012, 485(7400):651-5.
Oakley et al., "Intraneuronal beta-amyloid aggregates, neurodegeneration, and neuron loss in transgenic mice with five familial Alzheimer's disease mutations: potential factors in amyloid plaque formation," J. Neurosci., Oct. 2006, 26(40): 10129-40.

Obermeier et al., "Development, maintenance and disruption of the blood-brain barrier," Nature medicine, Dec. 2013, 19(12):1584.
Ohori et al., "Growth factor treatment and genetic manipulation stimulate neurogenesis and oligodendrogenesis by endogenous neural progenitors in the injured adult spinal cord," Journal of Neuroscience, Nov. 2006, 26(46):11948-60.
Okada et al., "Conditional ablation of Stat3 or Socs3 discloses a dual role for reactive astrocytes after spinal cord injury," Nature medicine, Jul. 2006, 12(7):829-34.
Ortinski et al., "Selective induction of astrocytic gliosis generates deficits in neuronal inhibition," Nat. Neurosci., May 2010, 13(5):584-91.
Osborn et al., "Astrogliosis: an integral player in the pathogenesis of Alzheimer's disease," Progress in Neurobiology, Sep. 2016, 144:121-41.
Ostrom et al., "CBTRUS statistical report: primary brain and central nervous system tumors diagnosed in the United States in 2008-2012," Neuro-oncology, Oct. 2015, 17(suppl_4):iv1-62.
Palop and Mucke, "Amyloid-β—induced neuronal dysfunction in Alzheimer's disease: from synapses toward neural networks," Nature neuroscience, Jul. 2010, 13(7):812-8.
Parkhurst et al., "Microglia promote learning-dependent synapse formation through brain-derived neurotrophic factor," Cell, Dec. 2013, 155(7):1596-609.
Paul et al., "Cystathionine γ-lyase deficiency mediates neurodegeneration in Huntington's disease," Nature, May 2014, 509(7498):96-100.
Pereira et al., "Direct reprogramming of resident NG2 glia into neurons with properties of fast-spiking parvalbumin-containing interneurons," Stem cell reports, Sep. 2017, 9(3):742-51.
Pla et al., "Dlx1 and Dlx2 promote interneuron GABA synthesis, synaptogenesis, and dendritogenesis," Cerebral Cortex, Nov. 2018, 28(11):3797-815.
Porter et al., "Conditional survival of all primary brain tumor patients by age, behavior, and histology," Neuroepidemiology, Jun. 2011, 36(4):230-9.
Pouladi et al., "Choosing an animal model for the study of Huntington's disease," Nat. Rev. Neurosci., Oct. 2013, 14(10):708-21.
Prinz and Priller, "Microglia and brain macrophages in the molecular age: from origin to neuropsychiatric disease," Nature Reviews Neuroscience, May 2014, 15(5):300-12.
Qin and Benveniste, "ELISA methodology to quantify astrocyte production of cytokines/chemokines in vitro," InAstrocytes, 2012 (pp. 235-249). Humana Press.
Querfurth and LaFerla, "Mechanisms of disease," N. Engl. J. Med., Jan. 2010, 362(4):329-44.
Rangel-Barajas and Rebec, "Dysregulation of corticostriatal connectivity in Huntington's disease: a role for dopamine modulation," Journal of Huntington's disease, Jan. 2016, 5(4):303-31.
Reidling et al., "Human neural stem cell transplantation rescues functional deficits in R6/2 and Q140 Huntington's disease mice," Stem cell reports, Jan. 2018, 10(1):58-72.
Reinius et al., "Conditional targeting of medium spiny neurons in the striatal matrix," Frontiers in behavioral neuroscience, Mar. 2015, 9:71.
Rexed, "A cytoarchitectonic atlas of the spinal coed in the cat," Journal of comparative neurology, Apr. 1954, 100(2):297-379.
Richardson et al., "Future applications: gene therapy," Neurosurgery Clinics, Apr. 2009, 20(2):219-24.
Richardson et al., "NG2-glia as multipotent neural stem cells: fact or fantasy?" Neuron, 70(4):661-673, May 2011.
Rikani et al., "The mechanism of degeneration of striatal neuronal subtypes in Huntington disease," Annals of neurosciences, Jul. 2014, 21(3):112.
Römer et al., "Plant pathogen recognition mediated by promoter activation of the pepper Bs3 resistance gene," Science, Oct. 2007, 318(5850):645-8.
Roome et al., "A reproducible Endothelin-1 model of forelimb motor cortex stroke in the mouse," Journal of neuroscience methods, Aug. 2014, 233:34-44.
Roybon et al., "GABAergic differentiation induced by Mash1 is compromised by the bHLH proteins Neurogenin2, NeuroD1, and NeuroD2," Cerebral cortex, May 2010, 20(5):1234-44.

(56) References Cited

OTHER PUBLICATIONS

Roybon et al., "Neurogenin2 directs granule neuroblast production and amplification while NeuroD1 specifies neuronal fate during hippocampal neurogenesis," PloS one, Mar. 2009, 4(3):e4779.
Sadleir et al., "Aβ reduction in BACE1 heterozygous null 5XFAD mice is associated with transgenic APP level," Molecular neurodegeneration, Dec. 2015, 10(1):1.
Sandhu et al., "Glutamic acid decarboxylase 67 haplodeficiency impairs social behavior in mice," Genes, Brain and Behavior, Apr. 2014, 13(4):439-50.
Sanjana et al., "Improved vectors and genome-wide libraries for CRISPR screening," Nat Methods, Aug. 2014, 11(8):783-784.
Santos et al., "Excitatory interneurons dominate sensory processing in the spinal substantia gelatinosa of rat," The Journal of physiology, May 2007, 581(1):241-54.
Sassone et al., "Regenerative approaches in Huntington's disease: from mechanistic insights to therapeutic protocols," Frontiers in neuroscience, Nov. 2018, 12:800.
Schmid et al., "Dysfunction of somatostatin-positive interneurons associated with memory deficits in an Alzheimer's disease model," Neuron, Oct. 2016, 92(1):114-25.
Schornack et al., "Gene-for-gene-mediated recognition of nuclear-targeted AvrBs3-like bacterial effector proteins," J. Plant Physiol., Feb. 2006, 163(3):256-72.
Shalem et al., "Genome-scale CRISPR-Cas9 knockout screening in human cells," Science, Jan. 2014, 343(6166):84-87.
Sheng et al., "Most tissue-resident macrophages except microglia are derived from fetal hematopoietic stem cells," Immunity, Aug. 2015, 43(2):382-93.
Silver and Miller, "Regeneration beyond the glial scar," Nature reviews neuroscience, Feb. 2004, 5(2):146-56.
Sofroniew, "Molecular dissection of reactive astrogliosis and glial scar formation," Trends in neurosciences, Dec. 2009, 32(12):638-47.
Srivastava and DeWitt, "In vivo cellular reprogramming: the next generation," Cell, Sep. 2016, 166(6):1386-96.
Stamouli and Politis, "Pro-inflammatory cytokines in Alzheimer's disease," Psychatrike= Psychiatriki, Oct. 2016, 27(4):264-75.
Sugio et al., "Two type III effector genes of Xanthomonas oryzae pv. oryzae control the induction of the host genes OsTFIIAγ1 and OsTFX1 during bacterial blight of rice," Proceedings of the National Academy of Sciences, Jun. 2007, 104(25):10720-5.
Takashima et al., "Prolonged inhibition of hepatocellular carcinoma cell proliferation by combinatorial expression of defined transcription factors," Cancer science, Nov. 2018, 109(11):3543-53.
Tong et al., "Astrocyte Kir4.1 ion channel deficits contribute to neuronal dysfunction in Huntington's disease model mice," Nature neuroscience, May 2014, 17(5):694-703.
Tsunemoto et al., "Diverse reprogramming codes for neuronal identity," Nature, May 2018, 557:375-380.
Tuszynski et al., "Neural stem cell dissemination after grafting to CNS injury sites," Cell, Jan. 2014, 156(3):388-9.
van Gijsel-Bonnello et al., "Metabolic changes and inflammation in cultured astrocytes from the 5xFAD mouse model of Alzheimer's disease: alleviation by pantethine," PloS one, Apr. 2017, 12(4):e0175369.
Venegas et al., "Microglia-derived ASC specks cross-seed amyloid-β in Alzheimer's disease," Nature, Dec. 2017, 552(7685):355-61.
Verret et al., "Inhibitory interneuron deficit links altered network activity and cognitive dysfunction in Alzheimer model," Cell, Apr. 2012, 149(3):708-21.

Wang et al., "The p53 pathway controls SOX2-mediated reprogramming in the adult mouse spinal cord," Cell reports, Oct. 2016, 17(3):891-903.
"Wang, ""Developing hippocampal delivery of AAV-NeuroD1 as a novel therapy for Alzheimer's disease," A Thesis in.
Molecular, Cellular and Integrative Biosciences, May 2016, 40 pages.
Wesson et al., "Olfactory dysfunction correlates with amyloid-β burden in an Alzheimer's disease mouse model," Journal of Neuroscience, Jan. 2010, 30(2):505-14.
Wu et al., "A chemical recipe for generation of clinical-grade striatal neurons from hESCs," Stem cell reports, Sep. 2018, 11(3):635-50.
Wu et al., "Tonic inhibition in dentate gyrus impairs long-term potentiation and memory in an Alzheimer's disease model," Nature communications, Jun. 2014, 5(1):1-3.
www.sciencemag.org [online], "Reprogrammed cells could tackle brain damage," Nov. 14, 2018, [retrieved on Jun. 25, 2019], retrieved from: URL<https://www.sciencemag.org/news/2018/11/reprogrammed-cell s-could-tackle-brain-damage>, 11 pages.
Xuan et al., "Genome-wide promoter extraction and analysis in human, mouse, and rat," Genome biology, Aug. 2005, 6(8):R72.
Yan et al., "A huntingtin knockin pig model recapitulates features of selective neurodegeneration in Huntington's disease," Cell, May 2018, 173(4):989-1002.
Yang et al., "CRISPR/Cas9-mediated gene editing ameliorates neurotoxicity in mouse model of Huntington's disease," The Journal of clinical investigation, Jun. 2017, 127(7):2719-24.
Yang et al., "Generation of pure GABAergic neurons by transcription factor programming," Nature methods, Jun. 2017, 14(6):621-8.
Yang et al., "Induced neuronal cells: how to make and define a neuron," Cell stem cell, Dec. 2011, 9(6):517-25.
Yang et al., "Os8N3 is a host disease-susceptibility gene for bacterial blight of rice," Proc. Natl. Acad. Sci. USA, Jul. 2006, 103(27):10503-10508.
Yang et al., "Towards a transgenic model of Huntington's disease in a non-human primate," Nature, Jun. 2008, 453(7197):921-4.
Yiu and He, "Glial inhibition of CNS axon regeneration," Nature Reviews Neuroscience, Aug. 2006, 7(8):617-27.
Yokoyama et al., "Molecular cloning of a human neuroD from a neuroblastoma cell line specifically expressed in the fetal brain and adult cerebellum," Molecular brain research, Nov. 1996, 42(1):135-9.
Zaiss et al., "Differential activation of innate immune responses by adenovirus and adeno-associated virus vectors," Journal of virology, May 2002, 76(9):4580-90.
Zernicka-Goetz et al., "Following cell fate in the living mouse embryo," Development, Mar. 1997, 124(6):1133-7.
Zhang et al., "Reversing glial scar back to neural tissue through NeuroD1-mediated astrocyte-to-neuron conversion," bioRxiv, Jan. 2018, 1:261438.
Zhao et al., "Neuronal transcription factors induce conversion of human glioma cells to neurons and inhibit tumorigenesis," PLoS One, Jul. 2012, 7(7):e41506.
Zhao et al., "The ASH1-miR-375-YWHAZ signaling axis regulates tumor properties in hepatocellular carcinoma," Molecular Therapy-Nucleic Acids, Jun. 2018, 11:538-53.
Zhao et al., "TRED: a Transcriptional Regulatory Element Database and a platform for in silico gene regulation studies," Nucleic acids research, Jan. 2005, 33(suppl_1):D103-7.
Zhuo et al., "Live astrocytes visualized by green fluorescent protein in transgenic mice," Developmental biology, Jul. 1997, 187(1):36-42.

* cited by examiner

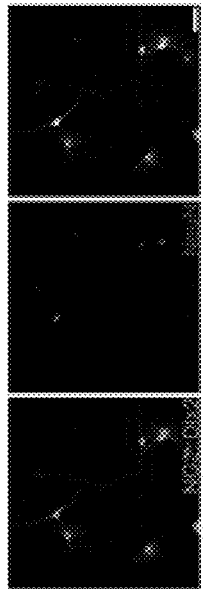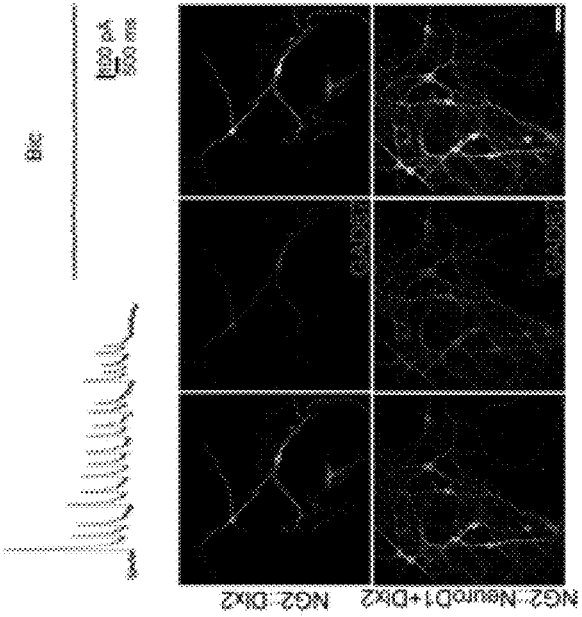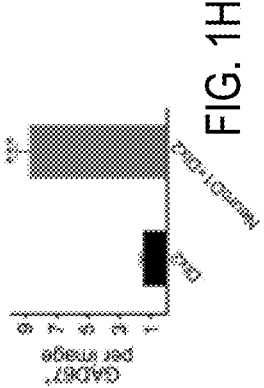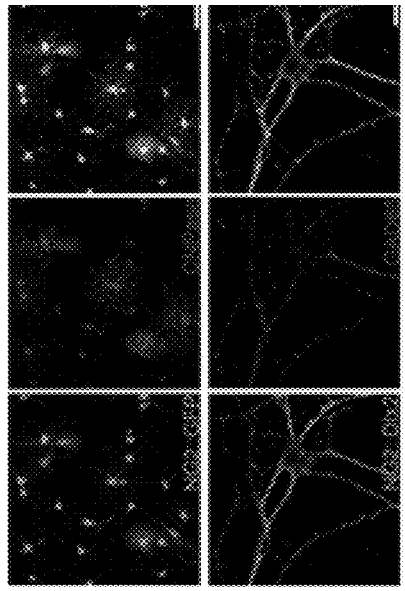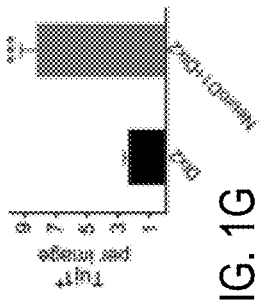

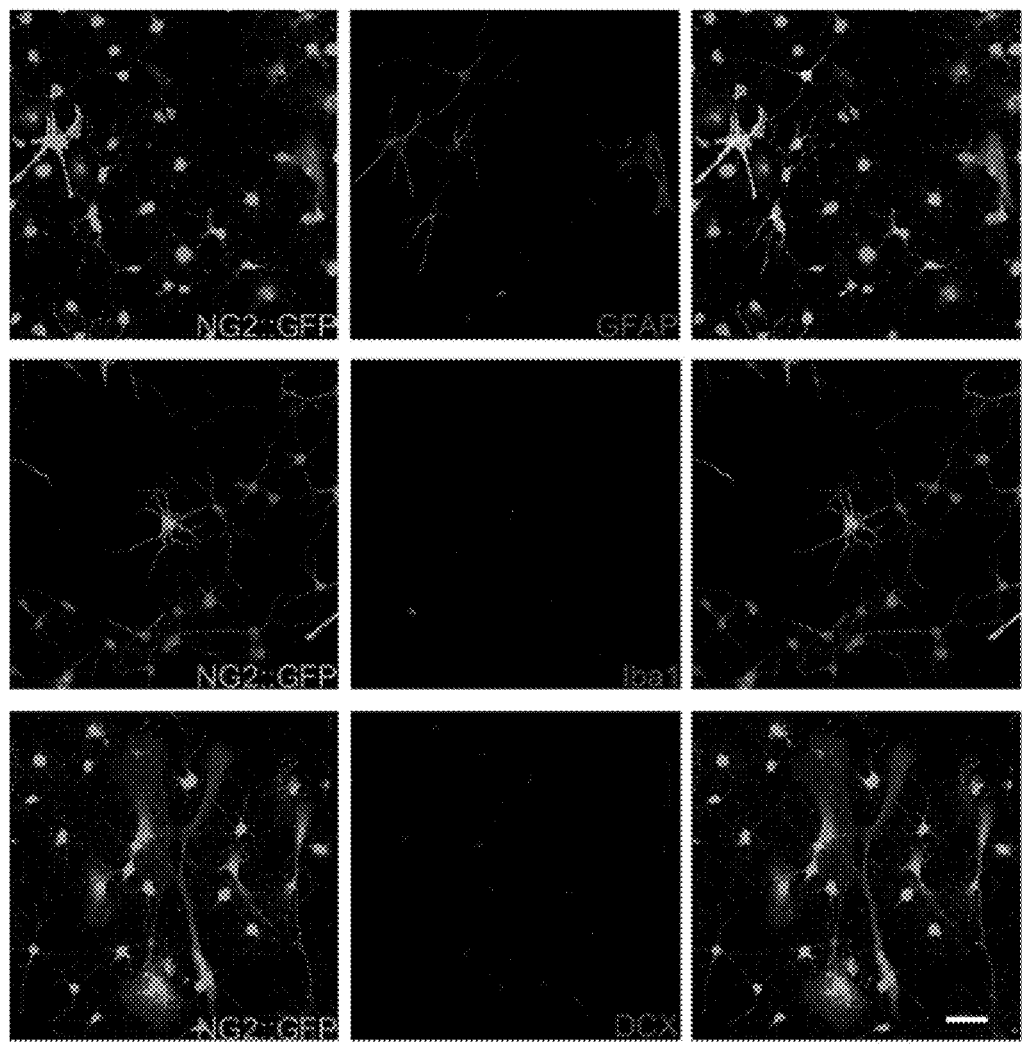
FIG. 2A
FIG. 2B
FIG. 2C
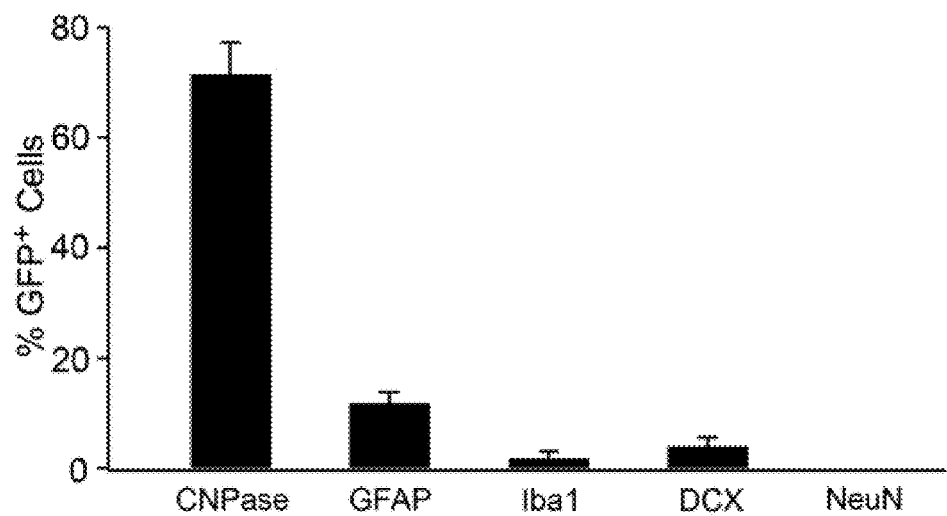
FIG. 2D

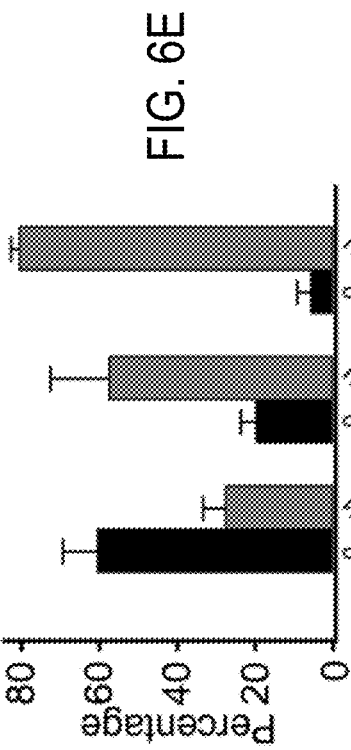
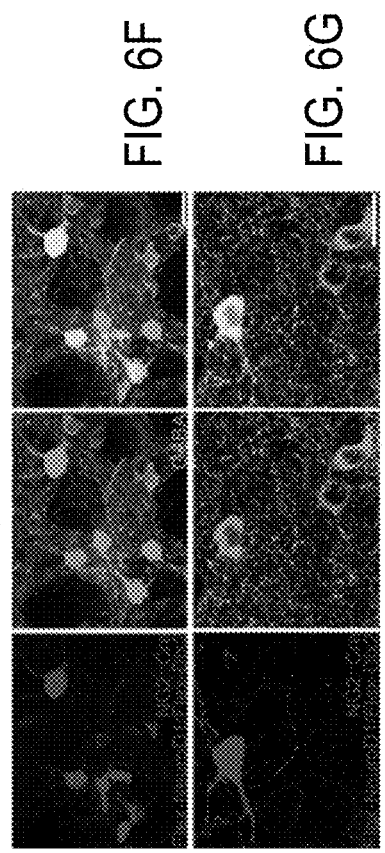
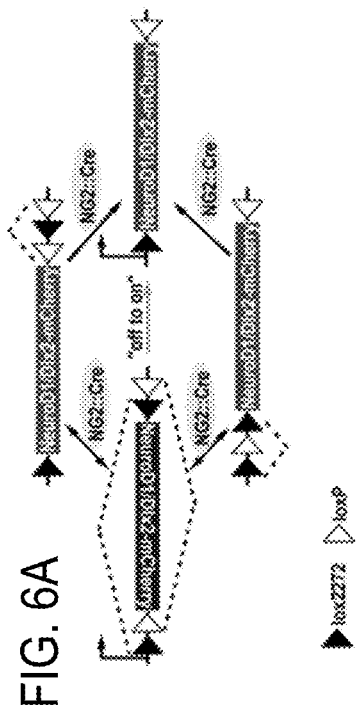
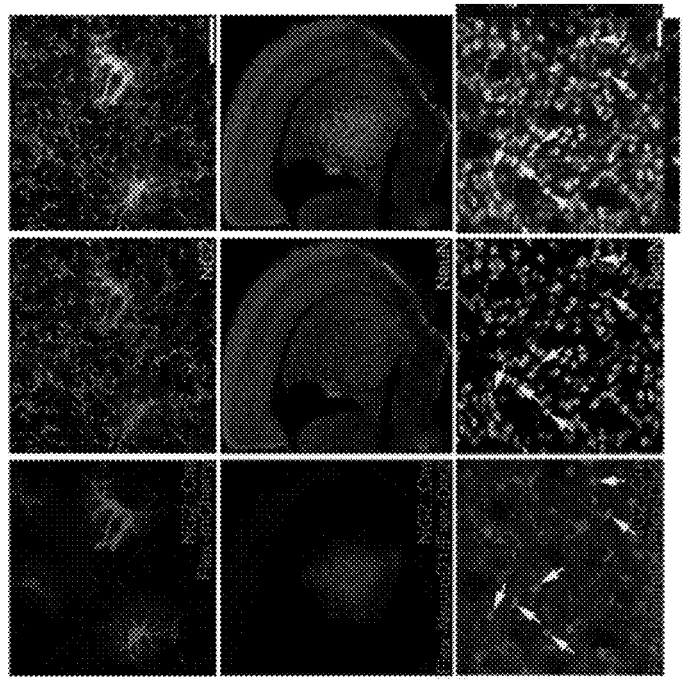

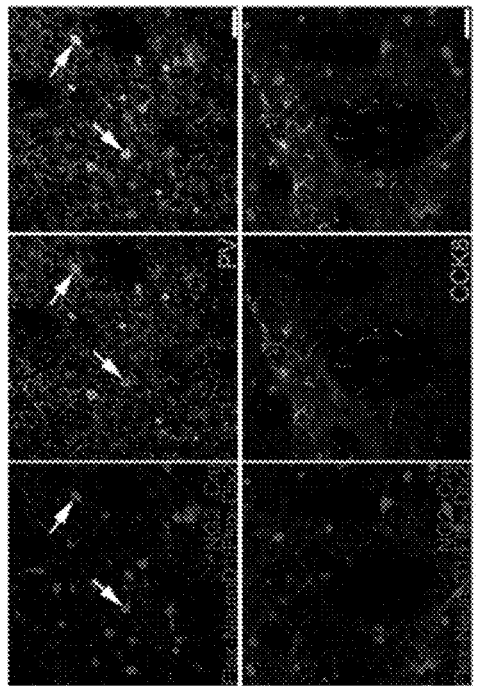
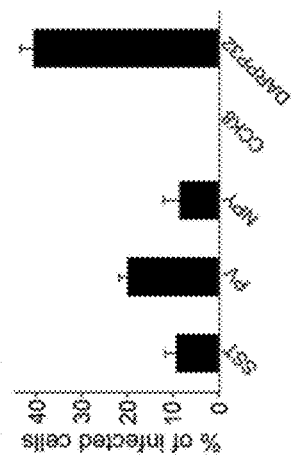
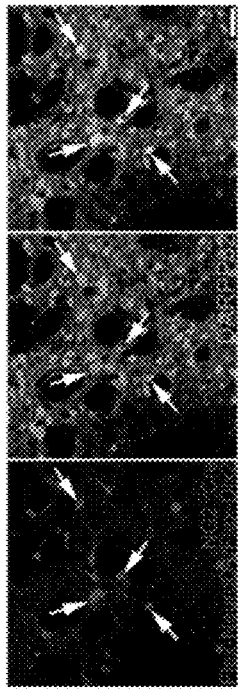
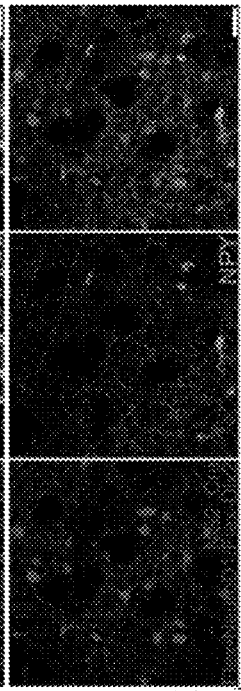
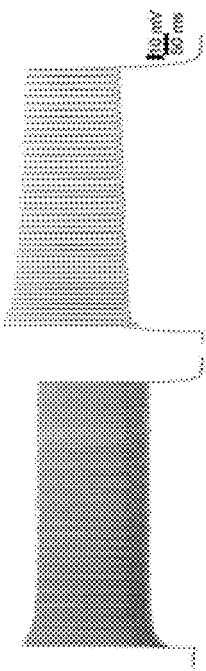
FIG. 8A  FIG. 8B  FIG. 8C  FIG. 8D  FIG. 8E  FIG. 8F  FIG. 8G

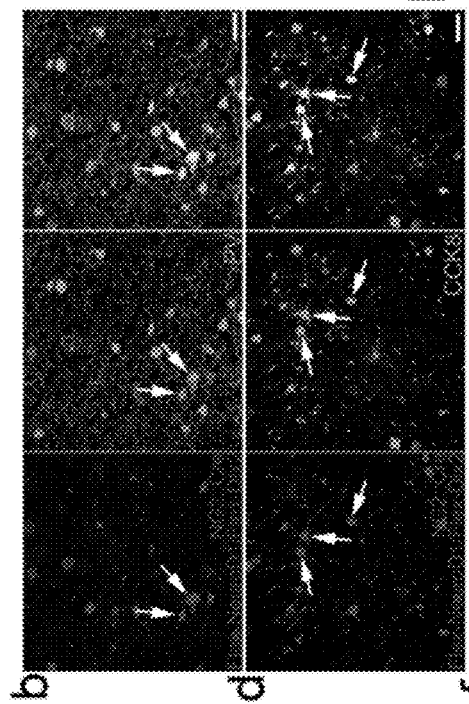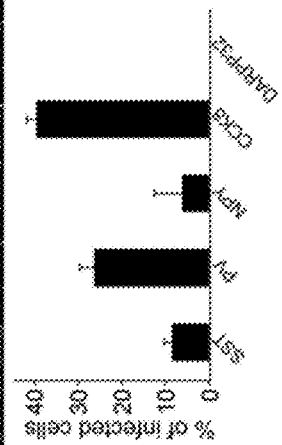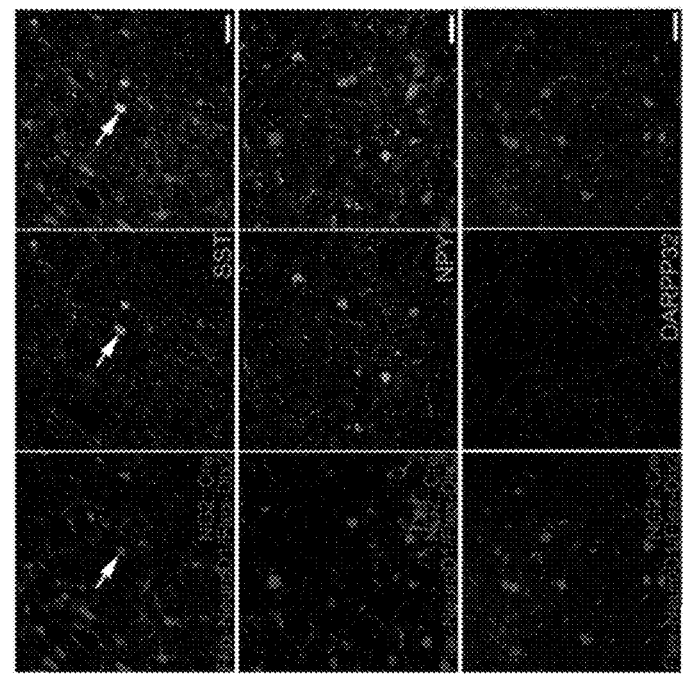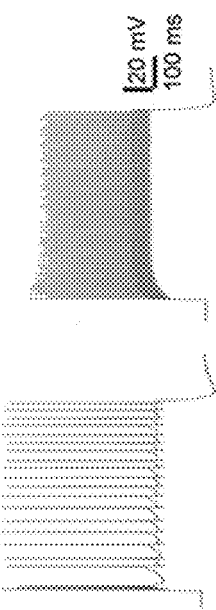
FIG. 10A  FIG. 10B  FIG. 10C  FIG. 10D  FIG. 10E  FIG. 10F  FIG. 10G

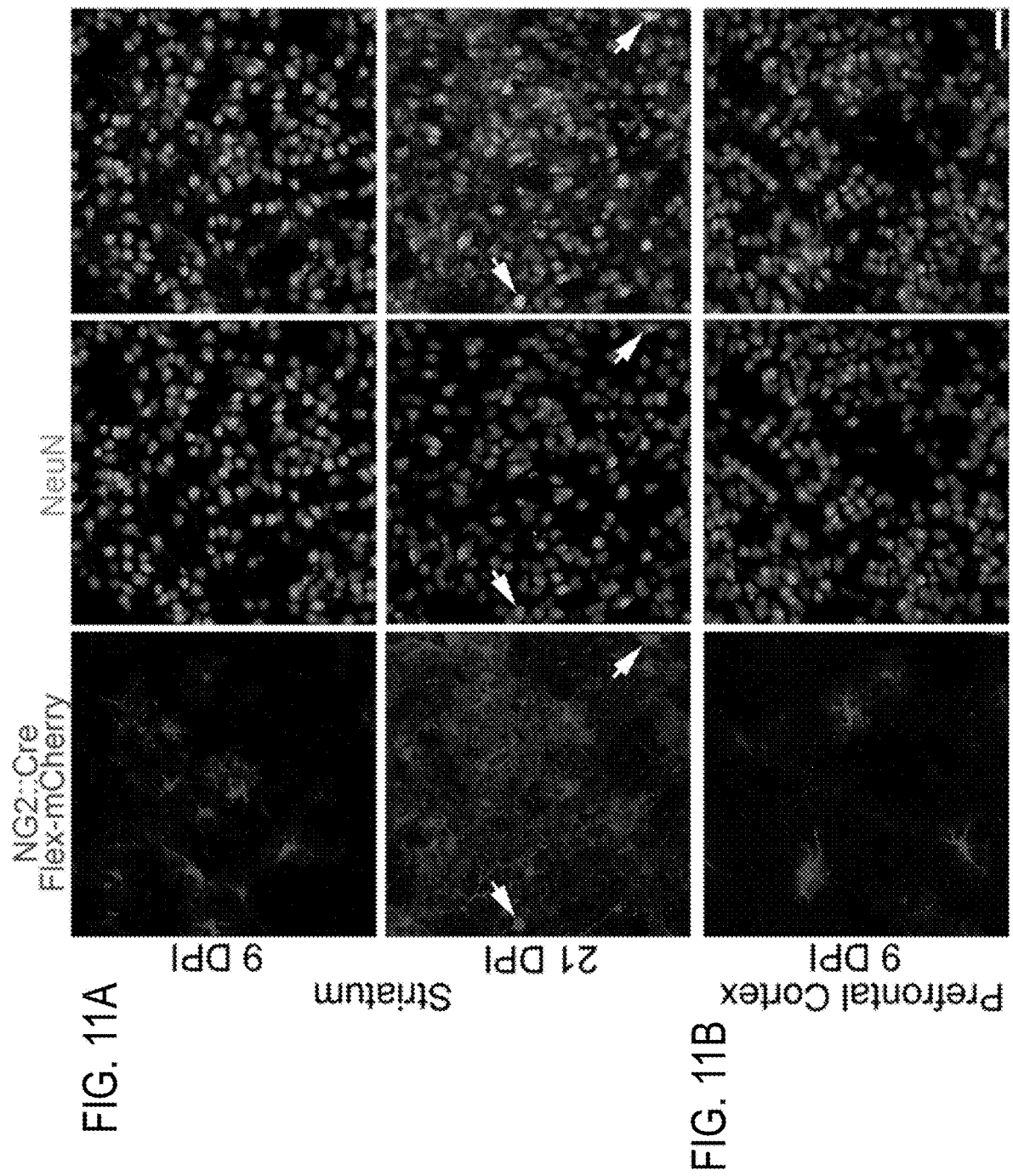

MTKSYSESGLMGEPQPQGPPSWTDECLSSQDEEHEADKKEDDLEAMNAEEDSLRNGGE
EEDEDEDLEEEEEEEEEDDDQKPKRRGPKKKKMTKARLERFKLRRMKANARERNRMH
GLNAALDNLRKVVPCYSKTQKLSKIETLRLAKNYIWALSEILRSGKSPDLVSFVQTLCKG
LSQPTTNLVAGCLQLNPRTFLPEQNQDMPPHLPTASASFPVHPYSYQSPGLPSPPYGTMD
SSHVFHVKPPPHAYSAALEPFFESPLTDCTSPSFDGPLSPPLSINGNFSFKHEPSAEFEKNY
AFTMHYPAATLAGAQSHGSIFSGTAAPRCEIPIDNIMSFDSHSHHERVMSAQLNAIFHD
(SEQ ID NO:1)

FIG. 12

MTGVFDSLVADMHSTQIAASSTYHQHQQPPSGGGAGPGGNSSSSSSLHKPQESPTLPVST
ATDSSYYTNQQHPAGGGGGGGSPYAHMGSYQYQASGLNNVPYSAKSSYDLGYTAAYT
SYAPYGTSSSPANNEPEKEDLEPEIRIVNGKPKKVRKPRTIYSSFQLAALQRRFQKTQYLA
LPERAELAASLGLTQTQVKIWFQNRRSKFKKMWKSGEIPSEQHPGASASPPCASPPVSAP
ASWDFGVPQRMAGGGGPGSGGSGAGSSGSSPSSAASAFLGNYPWYHQTSGSASHLQAT
APLLHPTQTPQPHHHHHHHGGGGAPVSAGTIF
(SEQ ID NO:2)

FIG. 13

GENERATING GABAERGIC NEURONS IN BRAINS

CROSS-REFERENCE TO RELATED APPLICATIONS

This application claims the benefit of U.S. Provisional Application Ser. No. 62/296,960, filed Feb. 18, 2016. The disclosure of the prior application is considered part of (and is incorporated by reference in) the disclosure of this application.

STATEMENT AS TO FEDERALLY SPONSORED RESEARCH

This invention was made with government support under Grant Nos. AG045656 and MH083911, awarded by the National Institutes of Health. The Government has certain rights in the invention.

BACKGROUND

1. Technical Field

This document relates to methods and materials for generating GABAergic neurons in brains. For example, this document relates to methods and materials for using nucleic acid encoding a NeuroD1 polypeptide and nucleic acid encoding a Dlx2 polypeptide to trigger glial cells (e.g., NG2 glial cells or astrocytes) within the brain (e.g., striatum) into forming GABAergic neurons (e.g., neurons resembling parvalbumin neurons or medium spiny neurons such as DARPP32-positive GABAergic neurons) that are functionally integrated into the brain of a living mammal (e.g., a human).

2. Background Information

Huntington's disease is mainly caused by mutations in the gene huntingtin (HTT), resulting into the expansion of trinucleotide CAG repeats that encode polyglutamine. When the number of CAG repeats in a huntingtin gene exceeds 36, it will cause disease, and the GABAergic medium spiny neurons in the striatum are in particular vulnerable to such polyglutamine toxicity (Ross et al., Lancet Neurol., 10:83-98 (2011); and Walker, Lancet, 369:218-228 (2007)). Currently, there is no effective treatment to cure Huntington's disease.

SUMMARY

This document provides methods and materials for generating GABAergic neurons in brains. For example, this document provides methods and materials for using nucleic acid encoding a NeuroD1 polypeptide and nucleic acid encoding a Dlx2 polypeptide to trigger glial cells (e.g., NG2 glial cells or astrocytes) within the brain (e.g., striatum) into forming GABAergic neurons (e.g., neurons resembling parvalbumin neurons or medium spiny neurons such as DARPP32-positive GABAergic neurons) that are functionally integrated into the brain of a living mammal (e.g., a human).

As described herein, nucleic acid designed to express a NeuroD1 polypeptide and nucleic acid designed to express a Dlx2 polypeptide can be delivered together to glial cells (e.g., NG2 glial cells or astrocytes) within a mammal's brain (e.g., striatum) in a manner that triggers the glial cells to form functional and integrated GABAergic neurons. These functional and integrated GABAergic neurons can resemble medium spiny neurons (e.g., they can be DARPP32-positive GABAergic neurons). Having the ability to form new GABAergic neurons within the striatum of a living mammal's brain using the methods and materials described herein can allow clinicians and patients (e.g., Huntington's disease patients) to create a brain architecture that more closely resembles the architecture of a healthy brain when compared to the architecture of an untreated Huntington's disease patient's brain following the significant death or degeneration of GABAergic medium spiny neurons. This can represent an important step forward for Huntington's disease patients even though there is currently no cure for the disease. In some cases, having the ability to replenish GABAergic medium spiny neurons within the striatum that die or degenerate during Huntington's disease progression using the methods and materials described herein can allow clinicians and patients to slow, delay, or reverse Huntington's disease progression.

In general, one aspect of this document features a method for forming GABAergic neurons in a striatum of a living mammal's brain. The method comprises, or consists essentially of, administering nucleic acid encoding a NeuroD1 polypeptide and nucleic acid encoding a Dlx2 polypeptide (or a NeuroD1 polypeptide and a Dlx2 polypeptide) to glial cells within the striatum, wherein the NeuroD1 polypeptide and the Dlx2 polypeptide are expressed by the glial cells, and wherein the glial cells form or are converted into GABAergic neurons within the striatum. The mammal can be a human. The glial cells can be NG2 glial cells or astrocytes. The GABAergic neurons can be parvalbumin-positive or DARPP32-positive. The NeuroD1 polypeptide can be a human NeuroD1 polypeptide. The Dlx2 polypeptide can be a human Dlx2 polypeptide. The nucleic acid encoding the NeuroD1 polypeptide can be administered to the glial cells in the form of a viral vector. In such cases, the viral vector can be an adeno-associated viral vector (e.g., an adeno-associated virus serotype 2 viral vector, an adeno-associated virus serotype 5 viral vector, or an adeno-associated virus serotype 9 viral vector). The nucleic acid encoding the Dlx2 polypeptide can be administered to the glial cells in the form of a viral vector. In such cases, the viral vector can be an adeno-associated viral vector (e.g., an adeno-associated virus serotype 2 viral vector, an adeno-associated virus serotype 5 viral vector, or an adeno-associated virus serotype 9 viral vector). The nucleic acid encoding the NeuroD1 polypeptide and the nucleic acid encoding the Dlx2 polypeptide can be located on the same viral vector, and the viral vector can be administered to the glial cells. In such cases, the viral vector can be an adeno-associated viral vector (e.g., an adeno-associated virus serotype 2 viral vector, an adeno-associated virus serotype 5 viral vector, or an adeno-associated virus serotype 9 viral vector). The nucleic acid encoding the NeuroD1 polypeptide and the nucleic acid encoding the Dlx2 polypeptide can be located on separate viral vectors, and each of the separate viral vectors can be administered to the glial cells. In such cases, each of the separate viral vectors can be an adeno-associated viral vector (e.g., an adeno-associated virus serotype 2 viral vector, an adeno-associated virus serotype 5 viral vector, or an adeno-associated virus serotype 9 viral vector). The administration can comprise a direct injection into the striatum of the living mammal's brain. The administration can comprise an intraperitoneal, intracranial, intravenous, intranasal, or oral administration. The nucleic acid encoding the NeuroD1 polypeptide can be operably linked to a promoter sequence; and the promoter sequence can be constitutive promoter sequence. The constitutive promoter sequence can comprise a NG2 promoter sequence, a GFAP promoter sequence, an EF1a promoter sequence, a CMV promoter sequence, an Aldh1L1 promoter sequence, or a CAG promoter sequence. The nucleic acid encoding the NeuroD1 polypeptide can be operably linked to a promoter sequence; and the promoter sequence can be a glial-specific promoter sequence. The glial-specific promoter sequence can comprise a NG2 promoter sequence, a GFAP promoter sequence, an Aldh1L1 promoter sequence, or an Olig2 promoter sequence. The nucleic acid encoding the Dlx2 polypeptide can be operably linked to a promoter sequence; and the promoter sequence can be constitutive promoter sequence. The constitutive promoter sequence can comprise a NG2 promoter sequence, a GFAP promoter sequence, an EF1a promoter sequence, a CMV promoter sequence, an Aldh1L1 promoter sequence, or a CAG promoter sequence. The nucleic acid encoding the Dlx2 polypeptide can be operably linked to a promoter sequence; and the promoter sequence can be a glial-specific promoter sequence. The glial-specific promoter sequence can comprise a NG2 promoter sequence, a GFAP promoter sequence, an Aldh1L1 promoter sequence, or an Olig2 promoter sequence.

In another aspect, this document features a composition for forming GABAergic neurons in a striatum of a living mammal's brain. The composition comprises, or consists essentially of, a nucleic acid vector comprising a nucleic acid sequence encoding a NeuroD1 polypeptide and a nucleic acid sequence encoding a Dlx2 polypeptide. The nucleic acid vector can be a viral vector such as an adeno-associated viral vector (e.g., an adeno-associated virus serotype 2 viral vector, an adeno-associated virus serotype 5 viral vector, or an adeno-associated virus serotype 9 viral vector). The nucleic acid sequence encoding the NeuroD1 polypeptide can be operably linked to a promoter sequence; and the promoter sequence can be constitutive promoter sequence. The constitutive promoter sequence can comprise a NG2 promoter sequence, a GFAP promoter sequence, an EF1a promoter sequence, a CMV promoter sequence, an Aldh1L1 promoter sequence, or a CAG promoter sequence. The nucleic acid sequence encoding the NeuroD1 polypeptide can be operably linked to a promoter sequence; and the promoter sequence can be a glial-specific promoter sequence. The glial-specific promoter sequence can comprise a NG2 promoter sequence, a GFAP promoter sequence, an Aldh1L1 promoter sequence, or an Olig2 promoter sequence. The nucleic acid sequence encoding the Dlx2 polypeptide can be operably linked to a promoter sequence; and the promoter sequence can be constitutive promoter sequence. The constitutive promoter sequence can comprise a NG2 promoter sequence, a GFAP promoter sequence, an EF1a promoter sequence, a CMV promoter sequence, an Aldh1L1 promoter sequence, or a CAG promoter sequence. The nucleic acid sequence encoding the Dlx2 polypeptide can be operably linked to a promoter sequence; and the promoter sequence can be a glial-specific promoter sequence. The glial-specific promoter sequence can comprise a NG2 promoter sequence, a GFAP promoter sequence, an Aldh1L1 promoter sequence, or an Olig2 promoter sequence.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIGS. 1A-H. Conversion of cultured NG2 cells into functional GABAergic neurons. (A) Differentiation of NG2 cells infected by control retrovirus (expressing GFP under NG2 promoter) into immature oligodendrocytes (CNPase-positive, red) after 3 days post-infection (DPI). (B) NG2 cells infected by NG2::Dlx2 retrovirus were reprogrammed into neurons (NeuN-positive, red, 7 DPI). (C) NG2-converted neurons were innervated by GABAergic synapses, as shown by GABAergic presynaptic protein GAD65 (red, 14 DPI). (D) Representative traces recorded from NG2-converted neurons showing upward spontaneous synaptic events when holding at −20 mV (14 DPI). Note all events were blocked by the $GABA_A$ receptor antagonist BIC (20 μM), suggesting that they were GABAergic events. (E-F) NeuroD1 enhanced the conversion efficiency induced by Dlx2, as shown by Tuj1 staining (E, 14 DPI) and GAD67 staining (F, 21 DPI). (G-H) Quantified data showing a significant increase of the number of Tuj1 positive neurons (G) or GAD67 positive GABAergic neurons (H) after coexpressing NeuroD1 with Dlx2 together. Data were presented as mean±s.e.m. ***P<0.001 (Student's t-test). Scale bars: 40 μm for panels A, B, E, and F; 10 μm for panel C.

FIGS. 2A-D. Characterizing mouse NG2 cultures. (A-C) Infecting mouse NG2 cultures with control retrovirus NG2::GFP revealed a small percentage of cells immunopositive for astrocyte marker GFAP, but not microglia marker Iba1 or immature neuron marker DCX. Scale bar: 40 μm. (D) Quantified data showing the majority of NG2 cells will differentiate into oligodendrocytes (CNPase) (3 days after infection of NG2::GFP in differentiation medium).

FIGS. 6A-H. In vivo reprogramming NG2 cells into functional GABAergic neurons. (A) Schematic diagram showing Cre-mediated FLEx switch of the NeuroD1/Dlx2-P2A-mCherry system. (B) NG2 cells detected after in vivo injection of NG2::Cre and FLEx-mCherry AAV into the striatum. (C) Macroscopic view of AAV-infected striatal region (21 DPI). (D) NeuroD1/Dlx2-infected NG2 cells showed neuron-like morphology and NeuN staining (arrow, red) at 21 days post AAV injection. (E) Quantified data showing a gradual decrease of NG2 cells among infected cells, accompanied by an increase of neurons after NeuroD1/Dlx2 infection, indicating a conversion of NG2 cells into neuronal cells. (F-G) NG2-converted neurons (21 DPI) in the striatum were immunopositive for GABA (F) and GAD67 (G). Scale bars: 40 µm for panel B, D; 20 µm for panel F, H. (H) Spontaneous synaptic events recorded from NG2-converted neurons (31 DPI).

FIGS. 8A-G. Characterizing the subtypes of NG2-converted neurons in striatum. (A-E) Immunostaining with a series of GABAergic neuron subtype markers (SST, PV, NPY, CCK8 and DARPP32) in the striatum after ectopic expression of NeuroD1 and Dlx2 in NG2 cells (21 DPI). Scale bars: 40 µm. (F) Quantified data showing a significant proportion of neurons immunopositive for DARPP32 and PV after NeuroD1/Dlx2 AAV injection into the striatum. (G) Representative traces showing action potential firing patterns recorded from NG2-converted neurons (31 DPI) in brain slices (n=20 neurons). Some neurons showed fast-spiking like firing pattern, with a frequency range of 70-200 Hz.

FIGS. 9A-F. In situ reprogramming cortical NG2 cells into functional GABAergic neurons. (A) NG2 cells revealed after injecting NG2::Cre and FLEx-mCherry AAV into mouse prefrontal cortex. (B) Low-magnification images showing AAV-infected site in the prefrontal cortex (21 DPI). (C) Reprogramming cortical NG2 cells into NeuN-positive neurons after ectopic expression of NeuroD1 and Dlx2 in NG2 cells (21 DPI). (D-E) Some NG2-converted neurons were immunopositive for GABA (D) and GAD67 (E) in the striatum (21 DPI). Scale bars: 40 µm for panels A, C; 500 µm for panel B; 20 µm for panels D, E. (F) Representative trace showing spontaneous synaptic events recorded from in situ NG2-converted neurons in the prefrontal cortex (35 DPI).

FIGS. 10A-G. Characterizing subtypes of NG2-converted neurons in prefrontal cortex. (A-E) Immunostaining showing different subtypes of GABAergic neurons among NG2-converted cells after NeuroD1/Dlx2 infection in the prefrontal cortex (21 DPI). Scale bars: 40 µm. (F) Quantified data showing a significant number of NG2-converted neurons in the prefrontal cortex being immunopositive for PV and CCK8. (G) Representative traces showing low and high frequency action potential firing patterns among NG2-converted neurons (35 DPI) in the prefrontal cortex (n=8 neurons). Note some neuron showed fast-spiking like action potential firing (138 Hz).

FIGS. 11A-B. Control virus infected mainly NG2 cells in the mouse brain. (A) Control AAV (NG2::Cre and FLEx-mCherry) infected mostly NG2 cells after injection into the striatum. (B) Control AAV (NG2::Cre and FLEx-mCherry) also infected mainly NG2 cells in the prefrontal cortex. Scale bar: 40 µm.

FIG. 12 is a listing of an amino acid sequence of a human NeuroD1 polypeptide (SEQ ID NO:1).

FIG. 13 is a listing of an amino acid sequence of a human Dlx2 polypeptide (SEQ ID NO:2).

DETAILED DESCRIPTION

Figure 3:
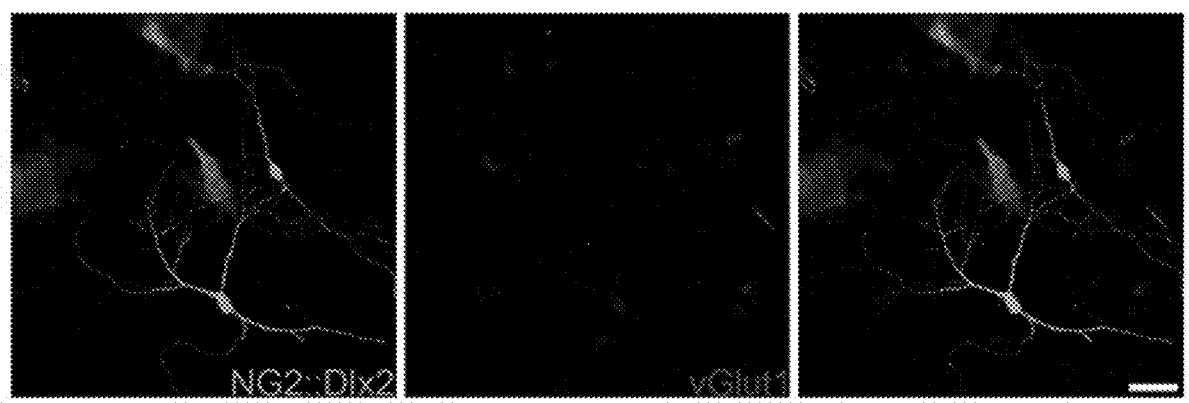
FIG. 3. No glutamatergic neurons generated from NG2 cells after expressing Dlx2. NG2-converted neurons were immunonegative for vGlut1, suggesting no glutamatergic neurons after reprogramming NG2 cells by Dlx2 alone (n=60 cells in 4 repeats). Scale bar: 40 μm.

This document provides methods and materials for generating GABAergic neurons in brains. For example, this document provides methods and materials for using nucleic acid encoding a NeuroD1 polypeptide and nucleic acid encoding a Dlx2 polypeptide to trigger glial cells within the brain into forming GABAergic neurons that can be functionally integrated into the brain of a living mammal. Forming GABAergic neurons as described herein can include converting glial cells within the brain into GABAergic neurons that can be functionally integrated into the brain of a living mammal. In some cases, the methods and materials described herein can be used to improve the brain architecture of Huntington's disease patient's brain such that it more closely resembles the brain architecture of a healthy human, to restore a healthy brain architecture to a Huntington's disease patient's brain, to reduce the progression of Huntington's disease, to delay the onset of Huntington's disease symptoms, and/or to treat Huntington's disease. In some cases, the methods and materials described herein can be used to reverse the effects of Huntington's disease in a mammal with Huntington's disease.

Any appropriate mammal can be treated as described herein. For example, mammals including, without limitation, humans, monkeys, dogs, cats, cows, horses, pigs, rats, and mice can be treated as described herein to generate GABAergic neurons in the brain of a living mammal. In some cases, a human having Huntington's disease can be treated as described herein to generate GABAergic neurons in a Huntington's disease patient's brain. A mammal can be identified as having Huntington's disease using any appropriate Huntington's disease diagnostic technique. For example, a genetic screen of the Huntingtin gene can be performed to diagnose a human as having Huntington's disease.

As described herein, a mammal can be treated by administering nucleic acid designed to express a NeuroD1 polypeptide and nucleic acid designed to express a Dlx2 polypeptide to glial cells (e.g., NG2 glial cells or astrocytes) within the mammal's brain (e.g., striatum) in a manner that triggers the glial cells to form functional and integrated GABAergic neurons. Examples of NeuroD1 polypeptides include, without limitation, those polypeptides having the amino acid sequence set forth in GenBank® accession number NP_002491 (GI number 121114306). A NeuroD1 polypeptide can be encoded by a nucleic acid sequence as set forth in GenBank® accession number NM_002500 (GI number 323462174). Examples of Dlx2 polypeptides include, without limitation, those polypeptides having the amino acid sequence set forth in GenBank® accession number NP_004396 (GI number 4758168). A Dlx2 polypeptide can be encoded by a nucleic acid sequence as set forth in GenBank® accession number NM_004405 (GI number 84043958).

Any appropriate method can be used to deliver nucleic acid designed to express a NeuroD1 polypeptide and nucleic acid designed to express a Dlx2 polypeptide to glial cells within the brain of a living mammal. For example, nucleic acid encoding a NeuroD1 polypeptide and nucleic acid encoding a Dlx2 polypeptide can be administered to a mammal using one or more vectors such as viral vectors. In some cases, separate vectors (e.g., one vector for nucleic acid encoding a NeuroD1 polypeptide, and one vector for nucleic acid encoding a Dlx2 polypeptide) can be used to deliver the nucleic acids to glial cells. In some cases, a single vector containing both nucleic acid encoding a NeuroD1 polypeptide and nucleic acid encoding a Dlx2 polypeptide can be used to deliver the nucleic acids to glial cells.

Vectors for administering nucleic acids (e.g., nucleic acid encoding a NeuroD1 polypeptide and nucleic acid encoding a Dlx2 polypeptide) to glial cells can be prepared using standard materials (e.g., packaging cell lines, helper viruses, and vector constructs). See, for example, *Gene Therapy Protocols* (*Methods in Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). Virus-based nucleic acid delivery vectors are typically derived from animal viruses, such as adenoviruses, adeno-associated viruses, retroviruses, lentiviruses, vaccinia viruses, herpes viruses, and papilloma viruses. In some cases, nucleic acid encoding a NeuroD1 polypeptide and nucleic acid encoding a Dlx2 polypeptide can be delivered to glial cells using adeno-associated virus vectors (e.g., an adeno-associated virus serotype 2 viral vector, an adeno-associated virus serotype 5 viral vector, or an adeno-associated virus serotype 9 viral vector), lentiviral vectors, retroviral vectors, adenoviral vectors, herpes simplex virus vectors, or poxvirus vector.

In addition to nucleic acid encoding a NeuroD1 polypeptide and/or nucleic acid encoding a Dlx2 polypeptide, a viral vector can contain regulatory elements operably linked to the nucleic acid encoding a NeuroD1 polypeptide and/or a Dlx2 polypeptide. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding a NeuroD1 polypeptide and/or a Dlx2 polypeptide. A promoter can be constitutive or inducible (e.g., in the presence of tetracycline), and can affect the expression of a nucleic acid encoding a polypeptide in a general or tissue-specific manner. Examples of tissue-specific promoters that can be used to drive expression of a NeuroD1 polypeptide and/or a Dlx2 polypeptide in glial cells include, without limitation, NG2, GFAP, Olig2, CAG, EF1a, Aldh1L1, and CMV promoters.

As used herein, "operably linked" refers to positioning of a regulatory element in a vector relative to a nucleic acid in such a way as to permit or facilitate expression of the encoded polypeptide. For example, a viral vector can contain a glial-specific NG2 promoter and nucleic acid encoding a NeuroD1 polypeptide or a Dlx2 polypeptide. In this case, the NG2 promoter is operably linked to a nucleic acid encoding a NeuroD1 polypeptide or a Dlx2 polypeptide such that it drives transcription in glial cells.

Nucleic acid encoding a NeuroD1 polypeptide and/or a Dlx2 polypeptide also can be administered to a mammal using non-viral vectors. Methods of using non-viral vectors for nucleic acid delivery are described elsewhere. See, for example, *Gene Therapy Protocols* (*Methods in Molecular Medicine*), edited by Jeffrey R. Morgan, Humana Press, Totowa, N.J. (2002). For example, nucleic acid encoding a NeuroD1 polypeptide and/or a Dlx2 polypeptide can be administered to a mammal by direct injection of nucleic acid molecules (e.g., plasmids) comprising nucleic acid encoding a NeuroD1 polypeptide and/or a Dlx2 polypeptide, or by administering nucleic acid molecules complexed with lipids, polymers, or nanospheres. In some cases, a genome editing technique such as CRISPR/Cas9-mediated gene editing can be used to activate endogenous NeuroD1 and/or Dlx2 gene expression.

Nucleic acid encoding a NeuroD1 polypeptide and/or a Dlx2 polypeptide can be produced by techniques including, without limitation, common molecular cloning, polymerase chain reaction (PCR), chemical nucleic acid synthesis techniques, and combinations of such techniques. For example, PCR or RT-PCR can be used with oligonucleotide primers designed to amplify nucleic acid (e.g., genomic DNA or RNA) encoding a NeuroD1 polypeptide and/or a Dlx2 polypeptide.

In some cases, NeuroD1 polypeptides and/or Dlx2 polypeptides can be administered in addition to or in place of nucleic acid designed to express a NeuroD1 polypeptide and/or nucleic acid designed to express a Dlx2 polypeptide. For example, NeuroD1 polypeptides and/or Dlx2 polypeptides can be administered to a mammal to trigger glial cells within the brain into forming GABAergic neurons that can be functionally integrated into the brain of the living mammal.

Nucleic acid designed to express a NeuroD1 polypeptide and nucleic acid designed to express a Dlx2 polypeptide (or NeuroD1 and/or Dlx2 polypeptides) can be delivered to glial cells within the brain (e.g., glial cells within the striatum) via direct intracranial injection, intraperitoneal administration, intranasal administration, intravenous administration, or oral delivery in nanoparticles and/or drug tablets, capsules, or pills.

As described herein, nucleic acid designed to express a NeuroD1 polypeptide and nucleic acid designed to express a Dlx2 polypeptide (or NeuroD1 and/or Dlx2 polypeptides) can be administered to a mammal (e.g., a human) having Huntington's disease and used to improve the brain architecture of the Huntington's disease patient's brain such that it more closely resembles the brain architecture of a healthy human, to restore a healthy brain architecture to a Huntington's disease patient's brain, to reduce the progression of Huntington's disease, to delay the onset of Huntington's disease symptoms, to treat Huntington's disease, or to reverse the effects of Huntington's disease in the mammal. In some cases, nucleic acid designed to express a polypeptide having the amino acid sequence set forth in SEQ ID NO:1 and nucleic acid designed to express a polypeptide having the amino acid sequence set forth in SEQ ID NO:2 (or a polypeptide having the amino acid sequence set forth in SEQ ID NO:1 and/or a polypeptide having the amino acid sequence set forth in SEQ ID NO:2) can be administered to a mammal (e.g., a human) having Huntington's disease as described herein and used to improve the brain architecture of the Huntington's disease patient's brain such that it more closely resembles the brain architecture of a healthy human, to restore a healthy brain architecture to a Huntington's disease patient's brain, to reduce the progression of Huntington's disease, to delay the onset of Huntington's disease symptoms, to treat Huntington's disease, or to reverse the effects of Huntington's disease in the mammal. For example, a single adeno-associated viral vector can be designed to express a polypeptide having the amino acid sequence set forth in SEQ ID NO:1 and a polypeptide having the amino acid sequence set forth in SEQ ID NO:2, and that designed viral vector can be administered to a human having Huntington's disease to treat Huntington's disease.

In some cases, a polypeptide containing the entire amino acid sequence set forth in SEQ ID NO:1, except that the amino acid sequence contains from one to ten (e.g., ten, one to nine, two to nine, one to eight, two to eight, one to seven, one to six, one to five, one to four, one to three, two, or one) amino acid additions, deletions, substitutions, or combinations thereof, can be used. For example, nucleic acid designed to express a polypeptide containing the entire amino acid sequence set forth in SEQ ID NO:1 with one to ten amino acid additions, deletions, substitutions, or combinations thereof and nucleic acid designed to express a Dlx2 polypeptide (or the polypeptides themselves) can be designed and administered to a human having Huntington's disease to treat Huntington's disease.

In some cases, a polypeptide containing the entire amino acid sequence set forth in SEQ ID NO:2, except that the amino acid sequence contains from one to ten (e.g., ten, one to nine, two to nine, one to eight, two to eight, one to seven, one to six, one to five, one to four, one to three, two, or one) amino acid additions, deletions, substitutions, or combinations thereof, can be used. For example, nucleic acid designed to express a polypeptide containing the entire amino acid sequence set forth in SEQ ID NO:2 with one to ten amino acid additions, deletions, substitutions, or combinations thereof and nucleic acid designed to express a NeuroD1 polypeptide (or the polypeptides themselves) can be designed and administered to a human having Huntington's disease to treat Huntington's disease. In another example, nucleic acid designed to express a polypeptide containing the entire amino acid sequence set forth in SEQ ID NO:1 with one to ten amino acid additions, deletions, substitutions, or combinations thereof and nucleic acid designed to express a polypeptide containing the entire amino acid sequence set forth in SEQ ID NO:2 with one to ten amino acid additions, deletions, substitutions, or combinations thereof can be designed and administered to a human having Huntington's disease to treat Huntington's disease.

Any appropriate amino acid residue set forth in SEQ ID NO:1 and/or SEQ ID NO:2 can be deleted, and any appropriate amino acid residue (e.g., any of the 20 conventional amino acid residues or any other type of amino acid such as ornithine or citrulline) can be added to or substituted within the sequence set forth in SEQ ID NO:1 and/or SEQ ID NO:2. The majority of naturally occurring amino acids are L-amino acids, and naturally occurring polypeptides are largely comprised of L-amino acids. D-amino acids are the enantiomers of L-amino acids. In some cases, a polypeptide as provided herein can contain one or more D-amino acids. In some embodiments, a polypeptide can contain chemical structures such as ε-aminohexanoic acid; hydroxylated amino acids such as 3-hydroxyproline, 4-hydroxyproline, (5R)-5-hydroxy-L-lysine, allo-hydroxylysine, and 5-hydroxy-L-norvaline; or glycosylated amino acids such as amino acids containing monosaccharides (e.g., D-glucose, D-galactose, D-mannose, D-glucosamine, and D-galactosamine) or combinations of monosaccharides.

Amino acid substitutions can be made, in some cases, by selecting substitutions that do not differ significantly in their effect on maintaining (a) the structure of the peptide backbone in the area of the substitution, (b) the charge or hydrophobicity of the molecule at particular sites, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of substitutions that can be used herein for SEQ ID NO:1 and/or SEQ ID NO:2 include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. Further examples of conservative substitutions that can be made at any appropriate position within SEQ ID NO:1 and/or SEQ ID NO:2 are set forth in Table 1.

TABLE 1

Examples of conservative amino acid substitutions.

| Original Residue | Exemplary substitutions | Preferred substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some embodiments, polypeptides can be designed to include the amino acid sequence set forth in SEQ ID NO:1 or SEQ ID NO:2 with the proviso that it includes one or more non-conservative substitutions. Non-conservative substitutions typically entail exchanging a member of one of the classes described above for a member of another class. Whether an amino acid change results in a functional polypeptide can be determined by assaying the specific activity of the polypeptide using, for example, the methods disclosed herein.

In some cases, a polypeptide having an amino acid sequence with at least 85% (e.g., 85%, 86%, 87%, 88%, 89%, 90%, 91%, 92%, 93%, 94%, 95%, 96%, 97%, 98%, or 99.0%) sequence identity to the amino acid sequence set forth in SEQ ID NO:1, provided that it includes at least one difference (e.g., at least one amino acid addition, deletion, or substitution) with respect to SEQ ID NO:1, can be used. For example, nucleic acid designed to express a polypeptide containing an amino acid sequence with between 90% and 99% sequence identity to the amino acid sequence set forth in SEQ ID NO:1 and nucleic acid designed to express a Dlx2 polypeptide (or the polypeptides themselves) can be designed and administered to a human having Huntington's disease to treat Huntington's disease.

In some cases, a polypeptide having an amino acid sequence with at least 85% (e.g., 85%, 86%, 87%, 88%, 89%, 90%, 91%, 92%, 93%, 94%, 95%, 96%, 97%, 98%, or 99.0%) sequence identity to the amino acid sequence set forth in SEQ ID NO:2, provided that it includes at least one difference (e.g., at least one amino acid addition, deletion, or substitution) with respect to SEQ ID NO:2, can be used. For example, nucleic acid designed to express a polypeptide containing an amino acid sequence with between 90% and 99% sequence identity to the amino acid sequence set forth in SEQ ID NO:2 and nucleic acid designed to express a NeuroD1 polypeptide (or the polypeptides themselves) can be designed and administered to a human having Huntington's disease to treat Huntington's disease. In another example, nucleic acid designed to express a polypeptide containing an amino acid sequence with between 90% and 99% sequence identity to the amino acid sequence set forth in SEQ ID NO:1 and nucleic acid designed to express a polypeptide containing an amino acid sequence with between 90% and 99% sequence identity to the amino acid sequence set forth in SEQ ID NO:2 (or the polypeptides themselves) can be designed and administered to a human having Huntington's disease to treat Huntington's disease.

Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

The percent sequence identity between a particular nucleic acid or amino acid sequence and a sequence referenced by a particular sequence identification number (e.g., SEQ ID NO:1 or SEQ ID NO:2) is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt-j c:\seg2.txt-p blastn-o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches by the length of the sequence set forth in the identified sequence (e.g., SEQ ID NO:1), followed by multiplying the resulting value by 100. For example, an amino acid sequence that has 340 matches when aligned with the sequence set forth in SEQ ID NO:1 is 95.5 percent identical to the sequence set forth in SEQ ID NO:1 (i.e., 340÷356×100=95.5056). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

The invention will be further described in the following examples, which do not limit the scope of the invention described in the claims.

EXAMPLES

Example 1—In Vivo Reprogramming Glial Cells into GABAergic Neurons in the Striatum to Treat Huntington's Disease NG2 Cell Culture As described elsewhere (Guo et al., *Cell Stem Cell*, 14:188-202 (2014)), mouse cortical tissue was dissected out and isolated from the brain of postnatal pups (P3-P5). Cortical cells were dissociated (0.25% trypsin-EDTA) and plated in 25 cm$^2$ flasks coated with poly-D-lysine (PDL, Sigma), and cultured in DMEM/F12 (GIBCO) with 10% fetal bovine serum (FBS, GIBCO) for 9 days, with the medium changed once every 3 days. On the ninth day, the flasks were rigorously shook, and the supernatant was collected and centrifuged to harvest NG2 cells with a small number of neurons, astrocytes, and microglial cells. The majority of astrocytes were flat and not easy to shake off the flasks. After centrifuge, cells were resuspended and seeded on PDL-coated coverslips (12 mm). The NG2 cells were maintained in serum-free DMEM medium (GIBCO) supplied with N2 supplements (STEMCELL), 10 ng/mL platelet-derived growth factor (PDGF, Invitrogen), 10 ng/mL FGF2 (Invitrogen), and 10 ng/mL EGF (Invitrogen), at 37° C. in humidified air with 5% $CO_2$.

Retrovirus Production

The human NG2 promoter gene was subcloned from hNG2 Promoter-GLuc (GeneCopoeia) and used to replace the CAG promoter in pCAG retroviral vector, which encoded either NeuroD1 or GFP, as described elsewhere (Guo et al., *Cell Stem Cell*, 14:188-202 (2014)), to generate pNG2-NeuroD1-IRES-GFP or pNG2-GFP-IRES-GFP. The mouse Dlx2 cDNA was subcloned from pCAG-Dlx2-IRES-DsRed (Heinrich et al., *PloS Biology*, (2010)) (obtained from Dr. Magdalena Götz) and inserted into pNG2 retroviral vector to generate pNG2-Dlx2-IRES-GFP. The E2A-Dlx2 cDNA was a PCR product from the template plasmid pCAG-Dlx2-IRES-DsRed using a 5' primer containing an E2A peptide. This PCR product was inserted into pNG2 retroviral vector to generate pNG2-NeuroD1-E2A-Dlx2-IRES-GFP. The pCAG-NeuroD1-IRES-GFP was constructed as described elsewhere (Guo et al., *Cell Stem Cell*, 14:188-202 (2014)). The human ASCL1 plasmid was constructed from a PCR product using a template of the pCMV6-XL5-ASCL1 (OriGene) that was inserted into a pCAG-GFP-IRES-GFP retroviral vector (Zhao et al., *J. Neurosci.*, (2006)) (obtained from Dr. Fred Gage) to generate pCAG-ASCL1-IRES-GFP. To package retroviral particles, the target plasmid described above were transfected into gpg helper-free human embryonic kidney (HEK) cells to generate vesicular stomatitis virus glycoprotein (VSV-G)-pseudotyped retroviruses encoding neural transcription factors. The titer of viral particles was about $10^7$ particles/mL, determined after transduction of HEK cells.

Trans-Differentiation of NG2 Cells into Neurons

Twenty-four hours after infection of mouse NG2 cells with retroviruses, the culture medium was replaced by a differentiation medium that included DMEM/F12 (GIBCO), 0.5% FBS (GIBCO), N2 supplements (GIBCO), vitamin C (VC, 5 µg/mL, Sigma), ROCK inhibitor (Y-27632, 1 µM, Selleckchem), and penicillin/streptomycin (GIBCO). To promote synaptic maturation during conversion, brain-derived neurotrophic factor (BDNF, 20 ng/mL, Invitrogen) was added to the cultures every four days. Due to the morphological change from NG2 cells to neurons during reprogramming, the empty space was filled with additional mouse astrocytes to support the functional development of converted neurons.

AAV Production

The hNG2 or hGFAP promoter was amplified by PCR and inserted into pAAV-MCS (Cell Biolab) between MluI and SacII to replace the CMV promoter. The Cre gene was obtained by PCR from hGFAP Promoter-Cre-MP-1 (Addgene) and inserted into pAAV-MCS EcoRI and SalI sites to generate pAAV-NG2::Cre and pAAV-GFAP::Cre. The Cre gene was subcloned into pAAV-MCS EcoRI and SalI sites to generate pAAV-NG2::Cre and pAAV-GFAP::Cre. To construct pAAV-FLEX-mCherry-P2A-mCherry (or pAAV-FLEX-GFP-P2A-GFP), pAAV-FLEX-NeuroD1-P2A-mCherry (or pAAV-FLEX-NeuroD1-P2A-GFP), and pAAV-FLEX-Dlx2-P2A-mCherry, the cDNAs coding NeuroD1, Dlx2, mCherry, or GFP were obtained by PCR using the retroviral constructs. The amplicons were fused with P2A-mCherry or P2A-GFP and subcloned into the pAAV-FLEX-GFP KpnI and XhoI sites. To generate pAAV-NG2::NeuroD1-P2A-GFP and pAAV-NG2::Dlx2-P2A-GFP, the proneural genes, NeuroD1 or Dlx2 fused with P2A-GFP, were subcloned into EcoRI and SalI sites after hNG2 promoter. Sequencing of the plasmid constructs was carried out to verify their identities.

AAV5 Production and Purification

Recombinant AAV5 was produced in 293AAV cells (Cell Biolabs). Briefly, polyethylenimine (PEI, linear, MW 25,000) was used for transfection of triple plasmids: the pAAV expression vector, pAAV5-RC (Cell Biolab) and pHelper (Cell Biolab). 72 hours post transfection, cells were scrapped in their medium and centrifuged, and frozen and thawed four times by placing it alternately in dry ice/ethanol and 37° C. water bath. AAV crude lysate was purified by centrifugation at 54,000 rpm for 1 hour in discontinuous iodixanol gradients with a Beckman SW55Ti rotor. The virus-containing layer was extracted, and viruses were concentrated by Millipore Amicon Ultra Centrifugal Filters. Virus titers were $1.2 \times 10^{12}$ GC/mL for GFAP::Cre and NG2::Cre, and $1.4 \times 10^{12}$ GC/mL for FLEx-NeuroD1-P2A-GFP, FLEx-NeuroD1-P2A-mCherry and FLEx-Dlx2-P2A-mCherry, and $1.6 \times 10^{12}$ GC/mL for FLEx-mCherry-P2A-mCherry, FLEx-GFP-P2A-GFP, NG2::NeuroD1-P2A-GFP and NG2::Dlx2-P2A-GFP were determined by QuickTiter™ AAV Quantitation Kit (Cell Biolabs).

Animals

All animals (C57/BL6 mice, 2-3 month old) were housed in a 12-hour light/dark cycle and fed with enough food and water.

Stereotaxic Viral Injection

Brain surgeries were conducted on 2-3 month-old C57/BL6 mice for AAV injection. The mice were anesthetized by injecting 20 mL/kg 2.5% Avertin (a mixture of 25 mg/mL of Tribromoethylethanol and 25 μL/ml T-amylalcohol) or ketamine/xylazine (120 mg/kg and 16 mg/kg) into the peritoneum and then placed in a stereotaxic setup. Artificial eye ointment was applied to cover the eye for protection purpose. The mice were operated with a midline scalp incision and were drilled with a hole (~1 mm) on the skull for needle injection, with its position relative to Bregma as following: AP +0.6 mm, ML 1.7 mm, DV −2.8 mm for striatum; AP +1.8 mm, ML 2.5 mm, DV −1.8 mm for prefrontal cortex. Each mouse received an injection of AAV using a 5 μL syringe and a 34G needle. The injection volume was 2 μL, and the flow rate was controlled at 0.2 μL/minute. After viral injection, the needle was kept in place for at least five additional minutes before slowly withdrawn.

Immunocytochemistry

For brain slice immunostaining, the animals were anesthetized with 2.5% Avertin and then quickly perfused with saline (0.9% NaCl) to wash away the blood followed with 4% paraformaldehyde (PFA) to fix the brains. The brains were then taken out and postfixed in 4% PFA overnight in cold room. After fixation, the samples were cut at 35 μm coronal sections by a vibratome (Leica), washed three times by PBS, and permeabilized in 0.3% Triton X-100 in phosphate-buffered saline (PBS, pH 7.4) for one hour. For GABA staining, the permeabilized step was skipped. All brain sections were blocked in blocking buffer (2.5% normal goat serum (NGS), 2.5% normal donkey serum (NDS), and 0.1% Triton X-100 in PBS) for another hour. For cell culture immunostaining, cells were fixed in 4% PFA in PBS for 12 minutes at room temperature. After fixation, the cultures were first washed three times by PBS and then permeabilized in 0.1% Triton X-100 in PBS for 30 minutes. All samples were blocked by blocking buffer for one hour before incubation with primary antibodies.

Primary antibodies, dissolved in blocking buffer, were incubated either with brain sections or culture samples overnight in cold room. After washing three times in PBS, the samples were incubated with appropriate secondary antibodies conjugated to DyLight 488, DyLight 594, Alexa Flour 647 and Cy3 (1:1000, Jackson ImmunoResearch) for one hour at room temperature, followed by extensive washing in PBS. Coverslips were finally mounted onto a glass slide with an anti-fading mounting solution with DAPI (Invitrogen). All images were taken by a confocal microscope (Olympus FV1000). Z-stacks of confocal images were acquired and analyzed using FV10-ASW 3.0 Viewer software (Olympus).

Antibodies

The following primary antibodies were used: polyclonal anti-green fluorescent protein (GFP, chicken, 1:2000, Abcam, AB13970), polyclonal anti-glial fibrillary acidic protein (GFAP, rabbit, 1:1000, Dako, Z0334), monoclonal anti-CNPase (mouse, 1:800, Abcam, AB6319), polyclonal anti-vesicular glutamate transporter 1 (vGluT1, rabbit, 1:1000, Synaptic Systems), monoclonal anti GAD67 (mouse, 1:1000, Millipore, MAB5406), monoclonal anti GAD65 (GAD-6, mouse, 1:1000, Developmental Studies Hybridoma Bank, Iowa City), monoclonal anti-NG2 (mouse, 1:600, Abcam, AB50009), polyclonal anti-Iba1 (rabbit, 1:1000, Wako, 019-19741), polyclonal anti-NeuN (rabbit, 1:1000, Millipore, ABN78), monoclonal anti-βIII tubulin (Tuj1, mouse, 1:1000, COVANCE, MMS-435P), polyclonal anti-γ-aminobutyric acid (GABA, rabbit, 1:2000, Sigma, A2052), polyclonal anti-Red Fluorescent Protein (RFP, rat, 1:1500, antibody-online, ABIN334653; and rabbit, 1:1000, Rockland, 600-401-379), polyclonal anti-T-box brain 1 (Tbr1, 1:800, rabbit, Abcam, AB31940), monoclonal anti-Ctip2 (Rat, 1:1000, Abcam, AB18465), monoclonal anti-NeuroD1 (mouse, 1:1000, Abcam, AB60704), polyclonal anti-Dlx2 (rabbit, 1:600, Abcam, AB30339), polyclonal anti-Doublecortin (DCX, rabbit, 1:1000, Abcam, AB18723), monoclonal anti-Parvalbumin (PV, mouse, 1:1000, sigma, P3088), polyclonal anti-Calretinin (CR, goat, 1:1500, Millipore, AB1550), monoclonal anti-Somatostatin (SST, rat, 1:300, Millipore, MAB354), polyclonal anti-Cholecystokinin (Catalog Nos. 26-33) (CCK-8, rabbit, 1:2000, sigma, C2581), polyclonal anti-Neuropeptide Y (NPY, rabbit, 1:2000, Abcam, AB30914), and polyclonal anti-Dopamine- and cAMP-regulated neuronal phosphoprotein (DARP-32, rabbit, 1:1500, Millipore, AB10518).

Image Analysis

Cell counts were performed by taking images of several randomly chosen views per coverslip or brain slice and analyzed by Image J software. Data were presented as mean±SEM. Student's t-test (paired or unpaired) was used for statistical analysis. *$P<0.05$, $P<0.01$, *$P<0.001$.

Electrophysiology

Patch-Clamp Recordings in Cell Cultures

Whole-cell recordings were conducted using Multiclamp 700A patch-clamp amplifier (Molecular Devices, Palo Alto, Calif.) as described elsewhere (Guo et al., *Cell Stem Cell*, 14:188-202 (2014)). The recording chamber was continuously perfused with a bath solution consisting of 128 mM NaCl, 30 mM glucose, 25 mM HEPES, 5 mM KCl, 1 mM $MgCl_2$, and 2 mM $CaCl_2$. The bath solution, with an osmolarity at 315-325 mOsm/L, was adjusted to pH 7.3 by NaOH. Patch pipettes were pulled from borosilicate glass (3-5 MΩ) and filled with an internal solution consisting of 125 mM KGluconate, 10 mM KCl, 10 mM Tris-phosphocreatine, 10 mM HEPES, 5 mM EGTA, 4 mM MgATP, and 0.5 mM $Na_2GTP$ (pH 7.3, adjusted with KOH) for recording action potentials. A different internal solution composed of 135 mM CsGluconate, 5 mM EGTA, 10 mM HEPES, 10 mM Tris-phosphocreatine, 4 mM MgATP, and 0.5 mM $Na_2GTP$ (pH 7.3, adjusted with KOH) was used for recording GABAergic synaptic responses (IPSCs). The series resistance was typically 15-30 MΩ and not compensated to avoid increased noise associated with compensation. $GABA_A$ receptor antagonist bicuculline (Bic) was applied through a gravity-driven drug delivery system (VC-6, Warner Hamden, Conn.). For voltage-clamp experiments, the membrane potential was typically held at −20 or 0 mV for recording upward IPSCs. Data were acquired using pClamp 9 software (Molecular Devices, Palo Alto, Calif.), sampled at 10 kHz, and filtered at 1 kHz. Action potentials were analyzed using pClamp 9 Clampfit software, and spontaneous synaptic events were analyzed using MiniAnalysis software (Synaptosoft, Decator, Ga.). All experiments were performed at room temperature.

Brain Slice Recordings

Brain slices were prepared at 1-1.5 month after AAV injection, and cut at 300 μm thick coronal sections with a Leica vibratome in ice-cold cutting solution (75 mM sucrose, 87 mM NaCl, 0.5 mM $CaCl_2$, 2.5 mM KCl, 7 mM $MgCl_2$, 1.25 mM $NaH_2PO_4$, 25 mM $NaHCO_3$, and 20 mM glucose). Slices were incubated in artificial cerebral spinal fluid (ACSF) containing: 119 mM NaCl, 2.5 mM KCl, 26 mM $NaHCO_3$, 1.25 mM $NaH_2PO_4$, 2.5 mM $CaCl_2$, 1.3 mM $MgCl_2$, and 10 mM glucose, and constantly bubbled with 95% $O_2$ and 5% $CO_2$ at 32-33° C. for 30 minutes. Brain slices were then transferred to a chamber at room temperature to recover for one hour. The recording chamber was set at 32-33° C. for all recordings. Whole-cell recordings were conducted using a pipette solution consisting of 135 mM K-Gluconate, 5 mM Na-phosphocreatine, 10 mM KCl, 2 mM EGTA, 10 mM HEPES, 4 mM MgATP, and 0.5 mM Na$_2$GTP (pH 7.3, adjusted with KOH, 290 mOsm/L). Pipette resistance was typically 4-6 MΩ, and series resistance was around 20-40 MΩ. The membrane potential was held at −70 mV when recording spontaneous events. Data were collected using pClamp 9 software (Molecular Devices, Palo Alto, Calif.), sampled at 10 kHz, and filtered at 1 kHz, then analyzed with pClamp 9 Clampfit and MiniAnalysis software (Synaptosoft, Decator, Ga.).

Reprogramming Cultured NG2 Cells into Functional GABAergic Neurons

NG2 cells are glial progenitor cells that mainly produce oligodendrocytes in both physiological and pathological conditions (Kang et al., Neuron, 68:668-681 (2010); Buffo et al., Proc. Natl. Acad. Sci. USA, 105:3581-3586 (2008); and Nishiyama et al., Nat. Rev. Neurosci., 10:9-22 (2009)). The following was performed to test whether Dlx2, a transcription factor critical for GABAergic fate determination, can reprogram NG2 cells into GABAergic neurons.

First, primary culture of mouse NG2 cells were used to test Dlx2 reprogramming capability. The cell cultures were enriched with NG2 cells, as demonstrated by successful infection with retrovirus expressing GFP under the control of human NG2 promoter (NG2::GFP-IRES-GFP). The majority of cells were immunopositive for oligodendrocyte marker CNPase (FIGS. 1A and 2D; 71.5±5.8% CNPase+; n=4 batches). In contrast, only about 10% of cells were GFAP-positive astrocytes, and none were NeuN-positive neurons (FIG. 2). The NG2 cultures were infected with retrovirus expressing Dlx2 under the control of NG2 promoter (NG2::Dlx2-IRES-GFP). Many Dlx2-infected NG2 cells became immunopositive for NeuN, a neuronal marker, after one week of infection (FIG. 1B; 57.1±5.1% NeuN+; n=5 batches; 7 DPI), suggesting that Dlx2 is capable of reprogramming NG2 cells into neuronal cells. Importantly, these NG2-reprogrammed neurons induced by Dlx2 exhibited many GABAergic synapses (FIG. 1C), but few glutamatergic synapses (FIG. 3), suggesting that NG2 cells are likely converted into GABAergic neurons but not glutamatergic neurons. To corroborate the immunostaining results, the functional properties of NG2-converted neurons were examined by patch-clamp recordings after two weeks of Dlx2 infection. Significant GABAergic synaptic events were detected in NG2-converted neurons (FIG. 1D; IPSC frequency, 0.7±0.2 Hz; amplitude, 19.6±3.7 pA; n=7; 14 DPI), which were mostly blocked by GABA$_A$ receptor antagonist bicuculline (BIC, 20 μM), confirming that NG2-converted neurons are GABAergic. Thus, Dlx2 can reprogram cultured NG2 cells into functional GABAergic neurons.

Co-Expression of NeuroD1 and Dlx2 Increases the Conversion Efficiency

Figure 4A:
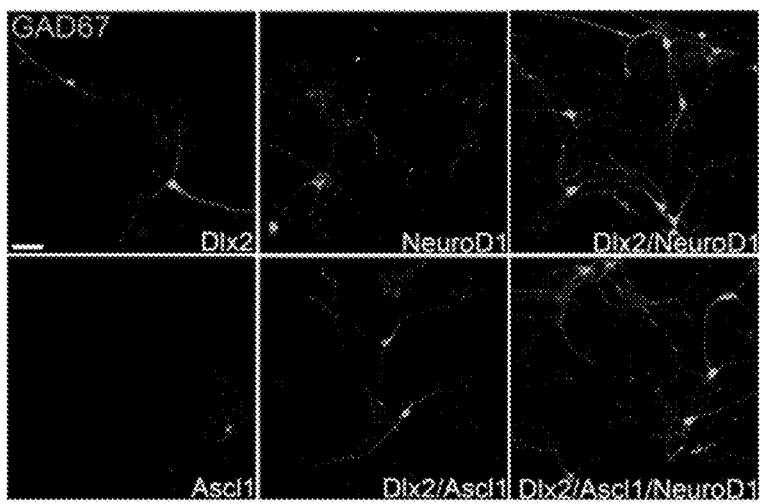
FIGS. 4A-D. Screening transcriptional factors for efficient conversion of NG2 cells into GABAergic neurons. (A) GAD67-positive neurons converted from NG2 cells after infection with different combinations of neural transcription factors (Dlx2, NeuroD1, and Ascl1; 14 DPI). (B) Quantified data showing a high conversion efficiency of NG2 cells into GABAergic neurons in Dlx2+NeuroD1 and Dlx2+NeuroD1+Ascl1 groups. (C) Representative traces showing upward GABAergic events recorded from NG2-converted neurons after infection with different transcription factors (21 days post infection). (D) Quantification of the frequency of GABAergic events also showed a high conversion efficiency of NG2 cells into GABAergic neurons by Dlx2+NeuroD1.
Figure 4B:
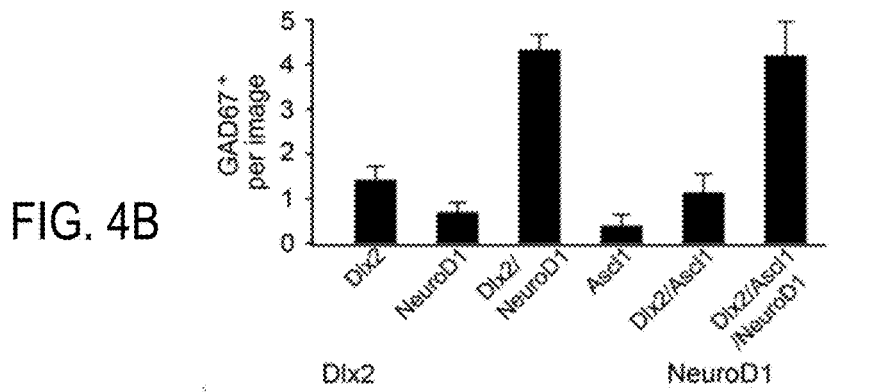
Figure 4C:
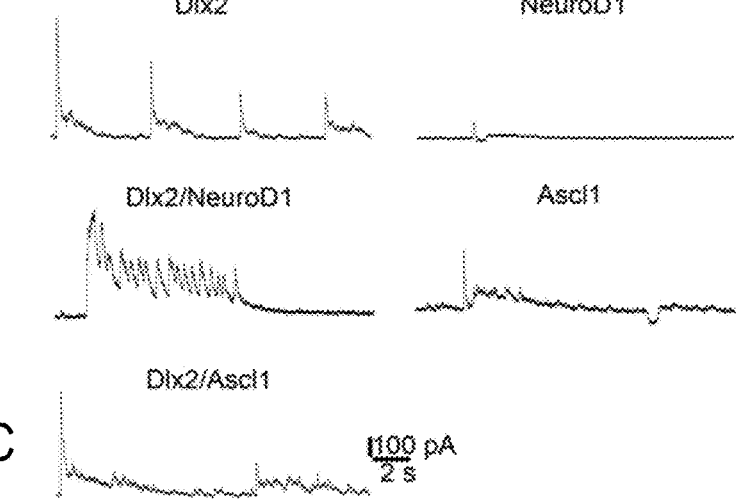
Figure 4D:
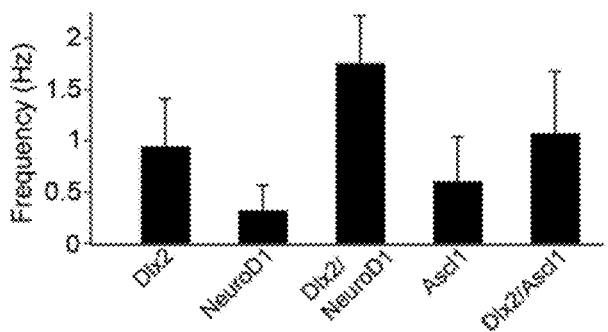

While Dlx2 alone was capable of reprogramming NG2 cells into GABAergic neurons, the reprogramming efficiency was not very high. To increase the reprogramming efficiency, other neural transcription factors such as Ascl1 (also known as Mash1; Vierbuchen et al., Nature, 463:1035-1041 (2010) and Bertrand et al., Nat. Rev. Neurosci., 3:517-530 (2002)) and NeuroD1 (Guo et al., Cell Stem Cell, 14:188-202 (2014) and Kuwabara et al., Nat. Neurosci., 12:1097-1105 (2009)), as well as combinations of Dlx2 with Ascl1 and NeuroD1, were tested (FIG. 4). Among all the combinations tested, co-overexpression of NeuroD1 and Dlx2 together generated the most number of GABAergic neurons (FIG. 4A-B, n=3 repeats, 14 DPI). Functional assay were used with electrophysiological recordings to analyze GABAergic events among different groups (FIG. 4C). The highest frequency of GABAergic events was also detected in the NeuroD1+Dlx2 group (FIG. 3D, n=3 repeats, 21 DPI), consistent with the immunostaining results.

A polycistronic retroviral vector expressing NeuroD1 and Dlx2 together under the control of NG2 promoter (NG2::NeuroD1-E2A-Dlx2-IRES-GFP) was constructed. The new retrovirus simultaneously expressing NeuroD1 and Dlx2 generated many more neurons than Dlx2 alone (FIG. 1E). Quantitatively, the Tuj1$^+$ neurons in the NeuroD1+Dlx2 group (8.2±1.0 cells/0.1 mm$^2$) were 3-fold more than that infected by Dlx2 alone (2.3±0.3 cells/0.1 mm$^2$; n=4 repeats; 12-14 DPI) (FIG. 1G). The conversion efficiency also increased from 57.2±8.8% by Dlx2 alone to 94.9±2.1% by NeuroD1+Dlx2 together. GAD67 staining was performed, which confirmed that the NeuroD1+Dlx2 converted neurons were mainly GABAergic (FIGS. 1F and 1H; NeuroD1+Dlx2, 8.8±0.9 cells/0.1 mm$^2$; Dlx2, 1.4±0.2 cells/0.1 mm$^2$; n=4 repeats; 19-21 DPI). Glutamatergic neurons were <3% after NeuroD1+Dlx2 conversion as revealed by VGlut1 staining (2.5±1.2%; n=4 repeats; 19-21 DPI). Therefore, NeuroD1 significantly facilitates Dlx2-mediated reprogramming of NG2 cells into functional GABAergic neurons.

NG2-Converted GABAergic Neurons have Specific Subtype Properties

Figure 5E:
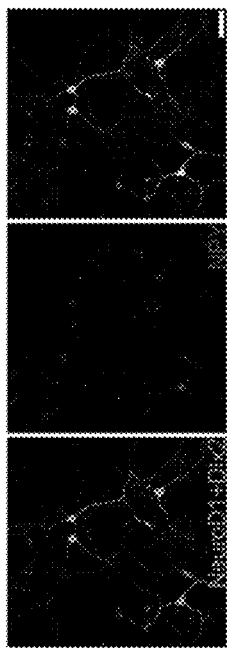
FIGS. 5A-H. Classification of NG2-converted GABAergic neurons in culture. (A-E) Immunostaining of NG2-converted neurons with a series of interneuron subtype markers (CR, SST, PV, CCK8 and NPY) after infection with NeuroD1+Dlx2 retroviruses (21 DPI). Scale bars: 40 μm. (F) Quantification showing that many NG2-converted neurons were immunopositive for calretinin (CR), somatostatin (SST), and parvalbumin (PV), but much less for CCK8 or NPY. (G-H) Representative traces showing different action potential firing patterns among NG2-converted neurons (G, 12.9 Hz; H, 38.9 Hz). Note that panel H shows an example of fast-spiking like firing pattern.
Figure 5F:
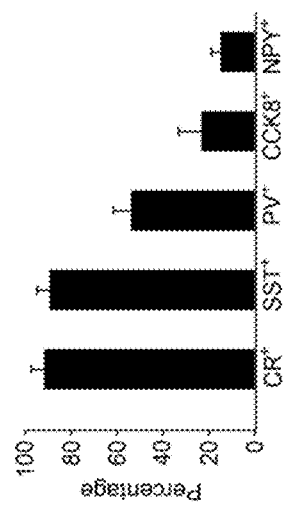
Figure 5G:
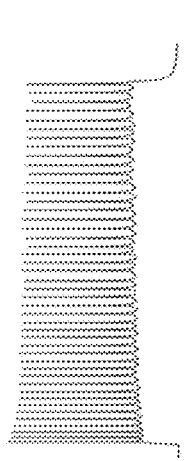
Figure 5H:
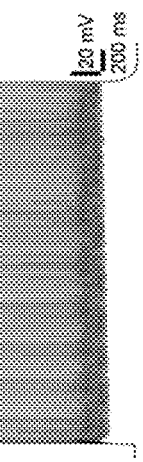
Figure 5A:
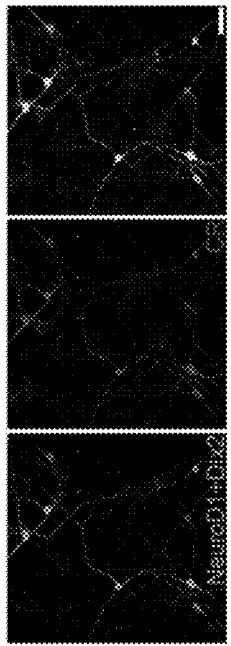
Figure 5B:
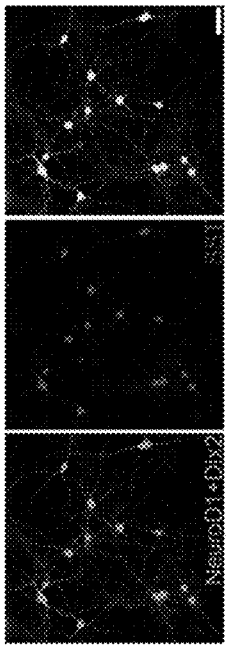
Figure 5C:
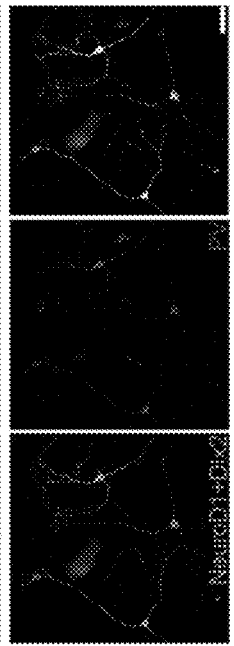
Figure 5D:
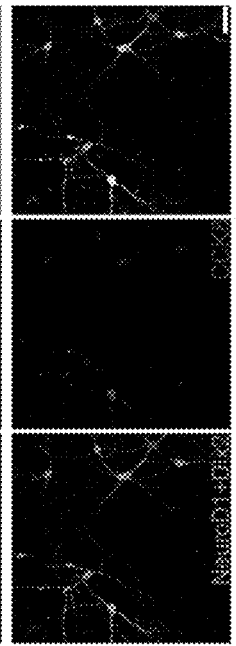

GABAergic interneurons have been classified into many subtypes according to specific protein expression markers, such as but not limited to calretinin (CR), parvalbumin (PV), somatostatin (SST), neuropeptide Y (NPY), and cholecystokinin (CCK) (Kepecs & Fishell, Nature, 505:318-326 (2014); Kawaguchi & Kondo, J. Neurocytol., 31:277-287 (2002); and Nat. Rev. Neurosci., 9:557-568 (2008)). Therefore, a series of immunostaining was performed with a variety of GABAergic markers to determine what specific subtypes of GABAergic neurons were converted from NG2 cells (FIG. 5). Interestingly, nearly 90% of NG2-converted neurons were immunopositive for CR or SST (FIG. 5A-B), over 50% were PV-positive (FIG. 5C), and less cells positive for CCK or NPY (FIG. 5D-E). Quantitative results were shown in FIG. 5F (CR, 91.8±5.6%; SST, 89.3±5.5%; PV, 53.9±7.8%; CCK8, 23.3±9.9%; NPY, 14.9±3.9%; n=3 batches; 19-21 DPI). GABAergic neurons also can be characterized according to their firing patterns, such as fast-spiking action potentials found in parvalbumin neurons (Markram et al., Nat. Rev. Neurosci., 5:793-807 (2004)). When analyzed the NG2-converted neurons with patch-clamp recordings, after NeuroD1-Dlx2 retroviral infection, some neurons fired fast-spiking like action potentials whereas others fired lower frequency action potentials (FIG. 5G-H, n=15 cells), supporting that NG2-converted neurons are a mixture of PV and non-PV interneurons. These results demonstrate that Dlx2 together with NeuroD1 can efficiently convert cultured NG2 cells into mature GABAergic neurons with a variety of subtypes, including PV, CR, and SST neurons.

In Vivo Reprogramming of NG2 Cells into Functional GABAergic Neurons

After reprogramming cultured NG2 cells into GABAergic neurons in vitro, the following was performed to examine whether NG2 cells in the mouse brain in vivo also can be converted into GABAergic interneurons. As demonstrated elsewhere (Guo et al., Cell Stem Cell, 14:188-202 (2014)), the in vivo reprogramming efficiency induced by retroviruses is not very high. In an attempt to overcome this, recombinant adeno-associated virus (serotype 5, rAAV5) were made for in vivo reprogramming. Among different serotypes of rAAV, rAAV5 was chosen for the majority of the experiments because it prefers to infect glial cells over neuronal cells (Howard et al., *Virology*, 372:24-34 (2008) and Markakis et al., *Mol. Ther.*, 18:588-593 (2010)). In order to specifically target NG2 cells and achieve stable transgene insertion, a Cre-FLEx (flip-excision) system, which includes a vector expressing Cre recombinase under the control of human NG2 promoter (NG2::Cre) and a vector with Cre-mediated FLEx switch of the inverted coding sequence of NeuroD1-P2A-mCherry or Dlx2-P2A-mCherry (FIG. 6A; Schnutgen et al., *Nat. Biotechnol.*, 21:562-565 (2003) and Atasoy et al., *J. Neurosci.*, 28:7025-7030 (2008)), was developed. The Cre-FLEx rAAV system was designed to allow Cre expression in NG2 cells, which in turn will activate the transcription of NeuroD1 or Dlx2 together with mCherry. For a control experiment, rAAV-NG2::Cre together with rAAV-FLEx-mCherry were first injected into the mouse striatum, a brain region enriched with GABAergic interneurons. Control rAAV (NG2::Cre and FLEx-mCherry) successfully infected NG2 cells in the striatum as revealed by NG2 immunostaining (FIG. 6B; 66.7±11.1% infected cells were NG2+; n=3 animals). Interestingly, after injecting rAAV-NG2::Cre plus rAAV-FLEx-NeuroD1 and rAAV-FLEx-Dlx2 into the striatum (FIG. 6C, Cre+NeuroD1+Dlx2), many infected cells were observed with neuron-like morphology and immunopositive for NeuN (FIG. 6D; 80.8±1.9% mCherry-labeled cells were also NeuN positive, n=4 animals; 21 DPI). To investigate the time course of NG2-neuron conversion, the percentage of NG2 cells versus neurons among the total number of viral infected cells (mCherry positive) from 4 to 21 days post viral injection (Cre+NeuroD1+Dlx2) was examined. Interestingly, a steady decrease of NG2 cells accompanied with a steady increase of Tuj1+ or NeuN+ neurons was observed during this conversion period (FIG. 6E), suggesting that NG2 cells are gradually converted into neurons.

Figure 7A:
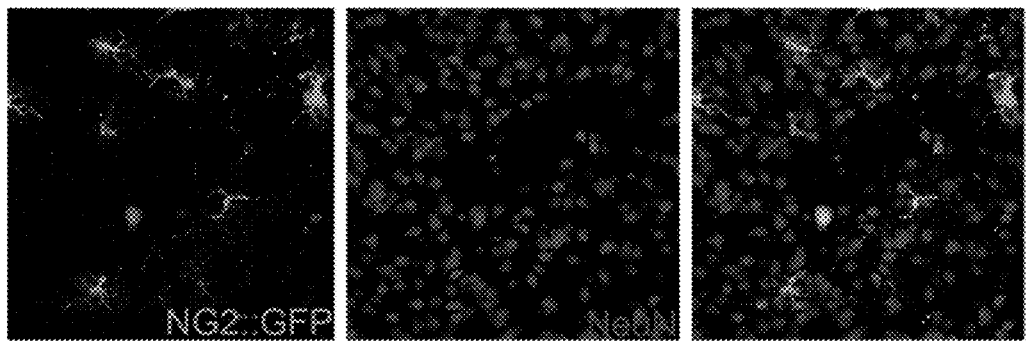
FIGS. 7A-C. Reprogramming NG2 cells into neurons under direct control of NG2 promoter. (A) NG2 cells revealed by infection of control virus NG2::GFP in the striatum. (B) NG2 cells became NeuN-positive neurons after infection by NG2::NeuroD1/Dlx2. Scale bar: 40 µm. (C) Quantified data showing the percentage of neurons versus NG2 cells after infection by NG2::GFP or NG2::NeuroD/Dlx2. The majority of NG2 cells converted into neurons after expressing NeuroD1+Dlx2 under the direct control of NG2 promoter.
Figure 7B:
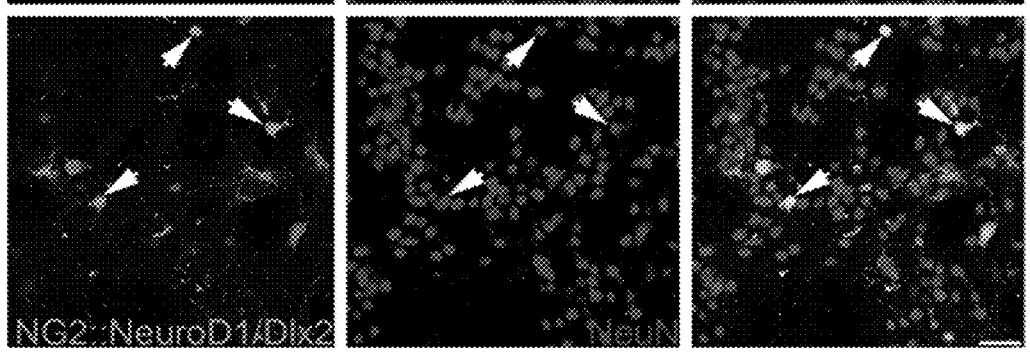
Figure 7C:
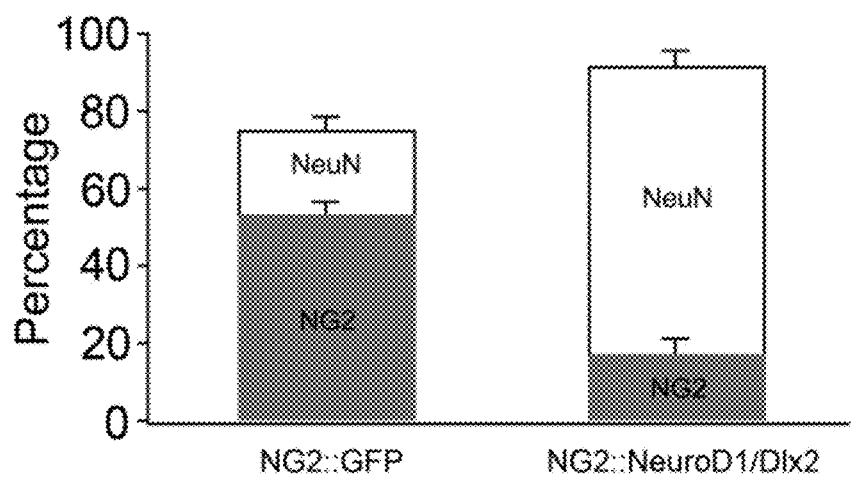

To further demonstrate direct conversion of NG2 glia into neurons, AAV5 vectors were constructed using NG2 promoter to directly drive the expression of NeuroD1 or Dlx2 (NG2::NeuroD1-P2A-GFP+NG2::Dlx2-P2A-GFP), without using Cre/FLEx system. Compared to GFP expression alone under the control of NG2 promoter (NG2::GFP), many more neurons (NeuN-positive) were detected after expressing NeuroD1+Dlx2 (FIG. 7). Therefore, NeuroD1 and Dlx2 together can efficiently reprogram NG2 cells into neuronal cells in the mouse brain in vivo. It is noted that the human NG2 promoter is not a specific promoter.

The following was performed to investigate whether NG2 cells in the striatum were converted into GABAergic neurons, as found in NG2 cell cultures. GABA and GAD67 immunostaining were performed, which confirmed that many NG2-converted neurons were indeed GABAergic neurons (FIG. 6F-G; 61.2±3.6% infected cells were GABA+; n=4 animals; 21 DPI). To test whether NG2-converted neurons were functionally connected with other neurons, brain slice recordings were performed at 1-1.5 months after NeuroD1+Dlx2 viral injection. The NG2-converted neurons exhibited robust spontaneous synaptic events (FIG. 6H; frequency, 6.8±1.3 Hz; amplitude, 13.3±0.9 pA; HP=−70 mV; n=16; 30-45 DPI). These results demonstrate that striatal NG2 cells can be reprogrammed into functional GABAergic neurons in situ after ectopic expression of NeuroD1 and Dlx2.

Regional Influence on the Subtypes of GABAergic Neurons

The subtypes of in vivo NG2-converted GABAergic neurons were further characterized using a series of GABAergic neuron markers (FIG. 8). In the striatum, medium spiny neurons are projecting neurons, not interneurons, but they are GABAergic neurons (Gangarossa et al., *Front Neural Circuits*, 7:22 (2013)). A significant proportion of NG2-converted neurons in the striatum were DARPP32-positive medium spiny neurons (FIG. 8A, 40.6±2.8%). Because medium spiny neurons are mostly sensitive to the toxic effects in Huntington's disease, this in vivo reprogramming method can be used as a new therapy to treat Huntington's disease by regenerating medium spiny neurons from internal glial cells. There also was a significant number of NG2-converted neurons immunopositive for PV (FIG. 8B), but rarely positive for CCK8 (FIG. 8C-D). Quantitatively, about 19.9±1.9% of NG2-converted neurons were PV+GABAergic neurons and 9.3±2.3% neurons were SST+ (FIG. 8F, n=3 animals), consistent with previous report that PV and SST neurons are the two major subtypes of interneurons in the striatum (Marin et al., *J. Neurosci.*, 20:6063-6076 (2000)). Functional analysis with brain slice recordings revealed that some NG2-converted neurons were capable of firing fast-spiking action potentials (FIG. 8G), indicating that they are likely PV interneurons. These results demonstrate that striatal NG2 cells can be reprogrammed in situ into DARPP32+ and PV+ GABAergic neurons by ectopic expression of Dlx2 and NeuroD1 together.

Figure 9A:
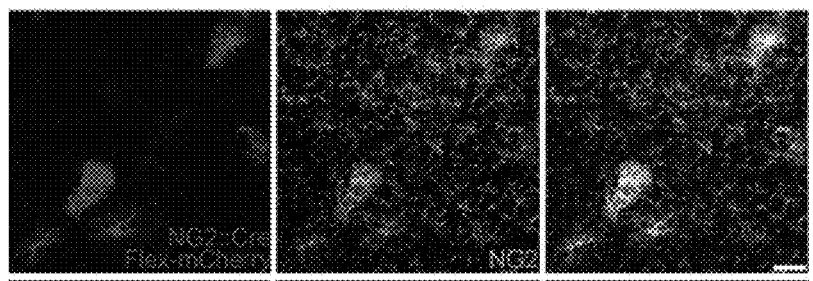
Figure 9C:
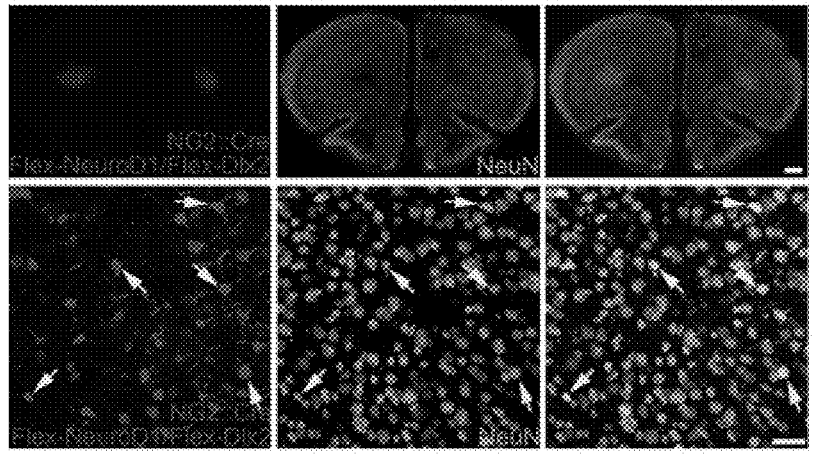
Figure 9F:
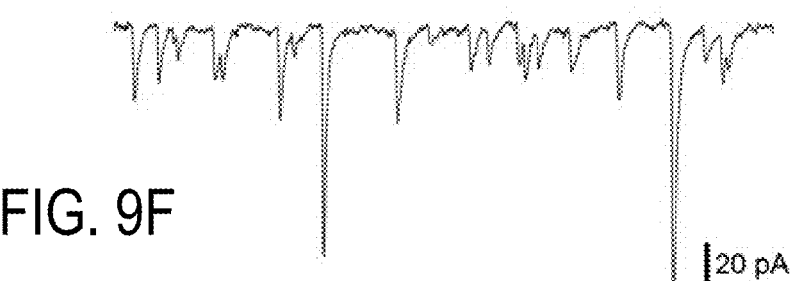
Figure 14:
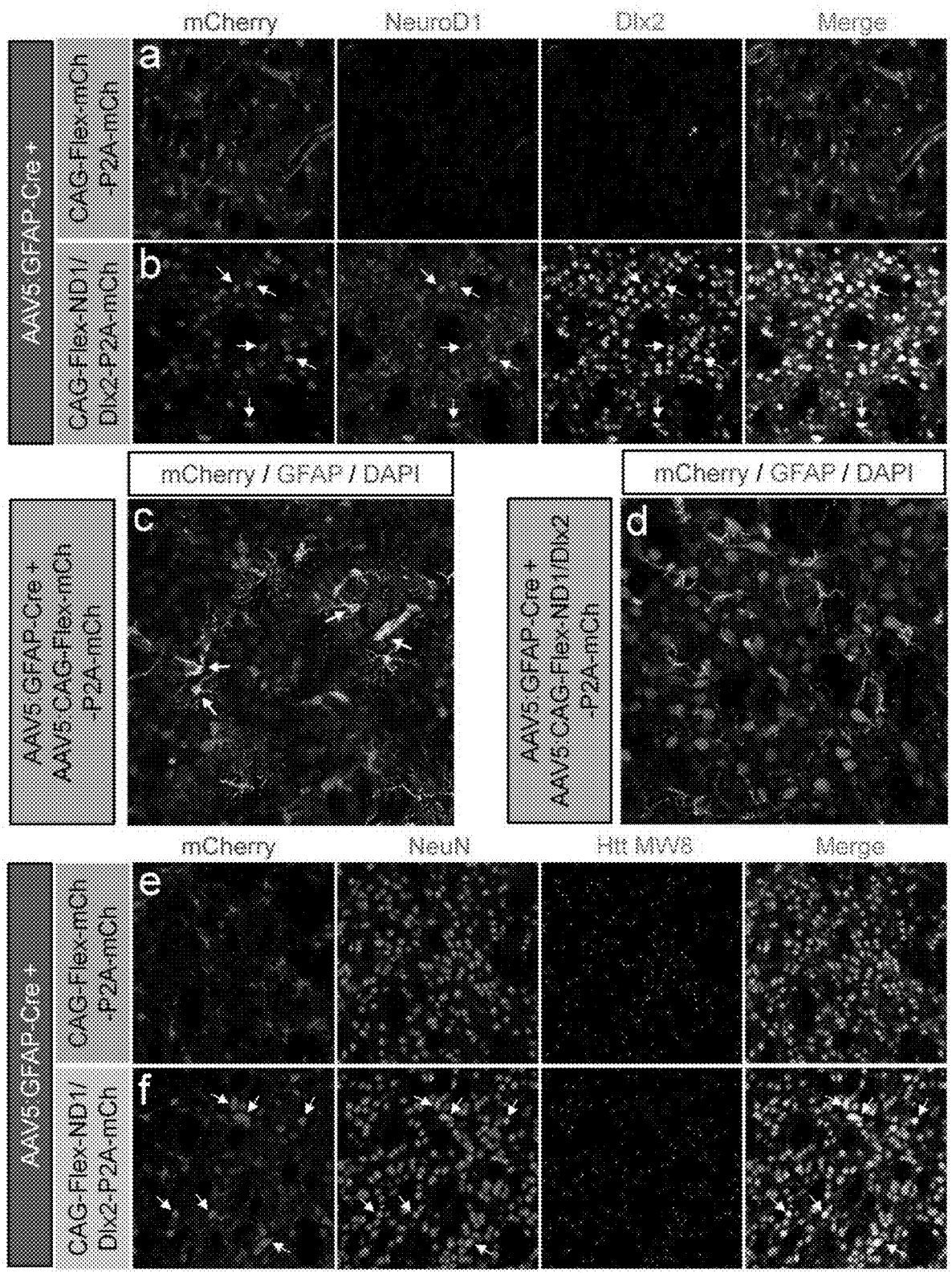
FIGS. 14A-F. NeuroD1 and Dlx2 mediate glia-to-neuron conversion in the striatum of R6/2 mice, a mouse model for Huntington's disease. (A, B) R6/2 mice were injected with AAV5 viruses expressing NeuroD1 and Dlx2 or mCherry control in astrocytes under the Cre-FLEx system. After 1 month, NeuroD1 (arrows) and Dlx2 (arrows) were detected in the infected cells (arrows) in NeuroD1/Dlx2 injected mice (B), but not in the mCherry control mice (A). (C) In the mCherry control group, the majority of infected cells were astrocytes labeled by GFAP (arrows). (D) In the NeuroD1/Dlx2 group, mCherry-positive cells were not co-localized with GFAP, but some exhibited a neuron-like morphology. (E, F) The NeuroD1/Dlx2-mediated glia-to-neuron conversion in R6/2 mouse striatum was confirmed by NeuN staining (arrows). The Htt aggregations in nucleus (co-localized with DAPI) were observed in both groups, confirming they were Huntington's disease mouse model mice.

The following was performed to investigate whether NG2 cells in different brain regions are reprogrammed into different subtypes of GABAergic neurons when using the same transcription factors NeuroD1+Dlx2. The same rAAV used in the striatum (NG2::Cre+FLEx-NeuroD1+FLEx-Dlx2) was injected into mouse prefrontal cortex, where the subtypes of GABAergic neurons are different from the striatum. As a control experiment, expression of mCherry alone (NG2::Cre+FLEx-mCherry) infected mainly NG2 cells in the prefrontal cortex (FIG. 9A, 77.5±1.3% infected cells were NG2+; n=3 animals; see, also, FIG. 11). In contrast, ectopic expression of Dlx2 and NeuroD1 in the NG2 cells of prefrontal cortex reprogrammed most of the NG2 cells into neurons (FIG. 9B-C; 72±1.1% mCherry+ cells were also NeuN+; n=3 animals; 21 DPI). Importantly, the majority of NG2-converted neurons also were immunopositive for GABA or GAD67 (FIG. 9D-E; 69.3±8% mCherry+ cells were also GAD67+; n=3 animals; 21 DPI), suggesting that they were GABAergic neurons. Moreover, brain slice recordings showed robust spontaneous synaptic events in the cortical NG2-converted neurons (FIG. 9F; frequency, 4.5±1.7 Hz; amplitude, 14.6±2.1 pA; n=7; 30-45 DPI), indicating that the NG2-converted neurons were functionally integrated into local neural circuits. Therefore, similar to striatal NG2 cells, cortical NG2 cells can be reprogrammed into functional GABAergic neurons by ectopic expression of Dlx2 and NeuroD1 together. However, different from the striatum where a large proportion of NG2-reprogrammed cells were DARPP32-positive medium spiny neurons, cortical NG2 cells were found to be reprogrammed into mainly CCK8 (39.7±2.2%, n=3 animals) or PV-positive neurons (26.3±3.4%, n=3 animals) (FIGS. 10B, 10D, and 10F), while fewer neurons were SST- or NPY-positive (FIGS. 10A and 10C). No DARPP32-positive cells were detected among cortical NG2-converted cell population (FIG. 10E-F). Patch-clamp recordings showed that cortical NG2-converted neurons also were capable of firing fast-spiking action potentials or lower frequency action potentials (FIG. 10G), confirming a mixture of different subtypes of GABAergic neurons converted from cortical NG2 cells. These results demonstrate that striatal and cortical NG2 cells can be reprogrammed into different subtypes of GABAergic neurons after expressing the same transcription factors Dlx2 and NeuroD1, indicating that either intrinsic lineage trace inside the regional glial cells or local environmental factors may regulate the fate choice of glia-neuron conversion.

Example 2—Regenerating Medium Spiny Neurons to Treat Huntington's Disease

A Huntington's disease (HD) mouse model, R6/2 transgenic mice, which carries 120 CAG repeats from human HD gene and exhibit disease onset at about 8-12 weeks of age is obtained. NeuroD1+Dlx2 AAV is injected into these HD mice at age of 6, 8, 10, and 12 weeks old to confirm that the in vivo reprogramming technology described herein extends the life of HD mice and improves the function of these HD mice. Injecting NeuroD1 and Dlx2 into the striatum of HD mice can have the ability to regenerate functional GABAergic neurons including medium spiny neurons, which in turn can increase the life span and rescue at least some of the functional deficits of HD mice.

Figure 15:
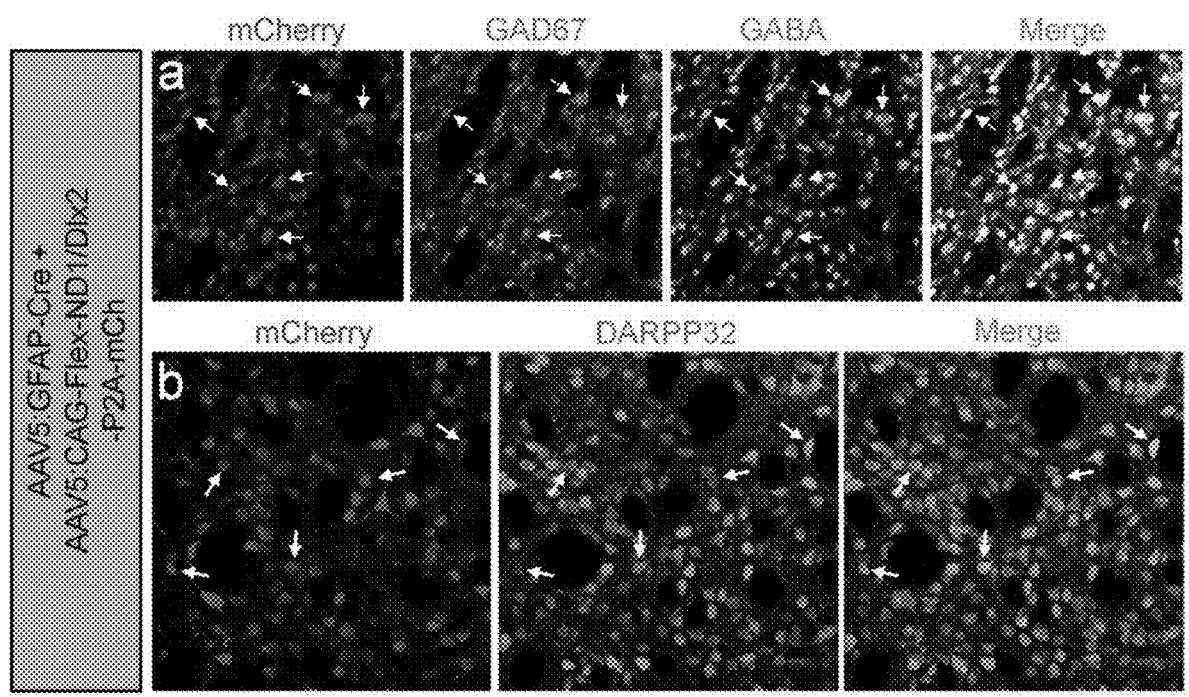
FIGS. 15A-B. Characterization of glia-converted neurons in the R6/2 mouse striatum. (A) NeuroD1/Dlx2-mediated glia-converted neurons (35 DPI) in R6/2 mouse striatum were immuno-positive for GAD67 (arrows) and GABA (arrows). (B) Some of the converted neurons also were labeled with DARPP32 (arrows), a marker for striatal medium spiny GABAergic neurons, demonstrating that the glia-converted neurons can replenish the lost DARPP32 neurons in Huntington's disease.
Figure 16:
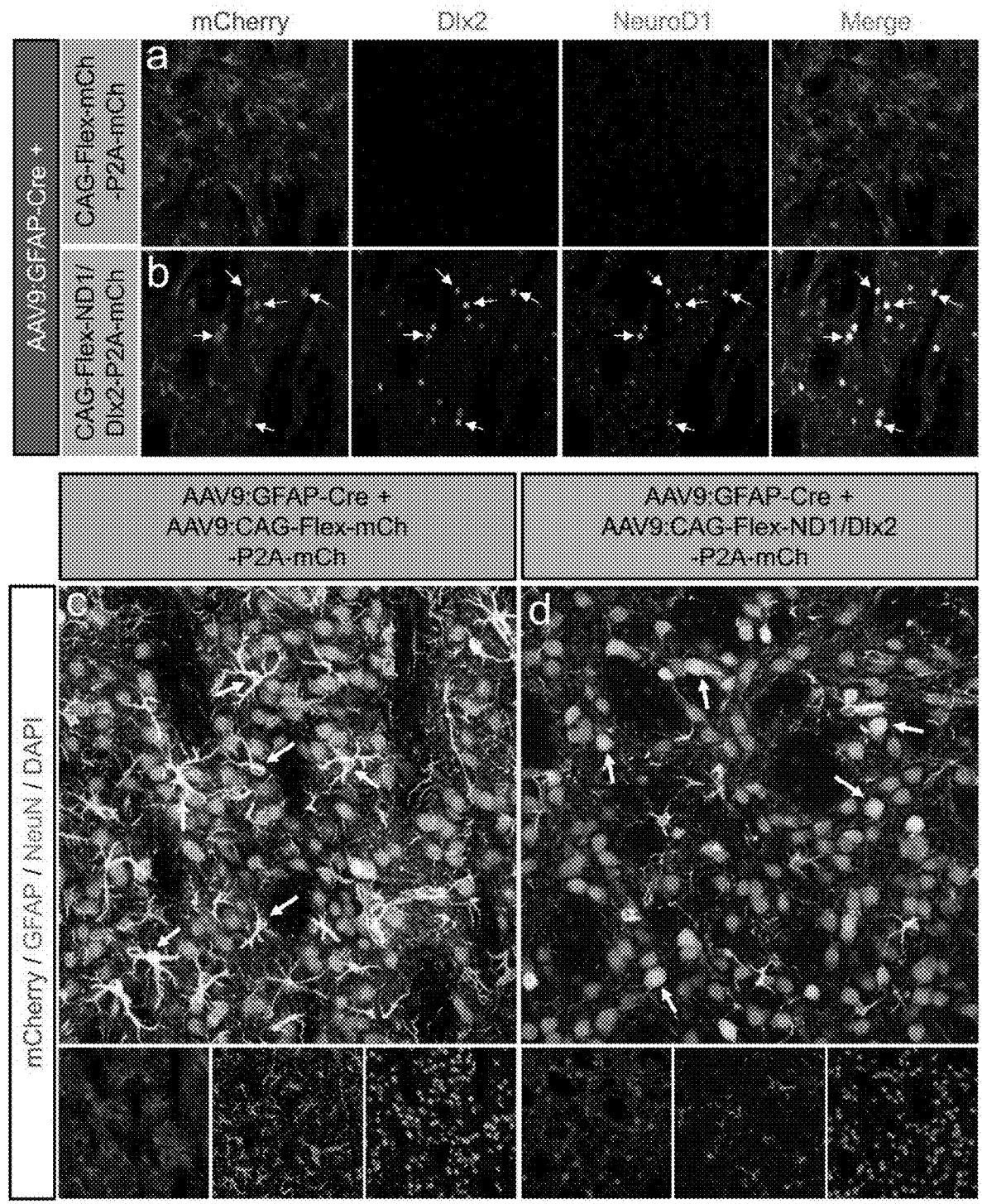
FIGS. 16A-D. NeuroD1 and Dlx2 expressed using AAV9 viral vectors mediate glia-to-neuron conversion in the striatum of R6/2 mice, a mouse model for Huntington's disease. (A, B) AAV9 was injected into the striatum, and Dlx2 and NeuroD1 were detected in the infected cells at 10 days post injection (arrows). (C) In the mCherry control group, the majority of infected cells were co-localized with astrocytic marker GFAP (arrows). (D) In the NeuroD1/Dlx2 group, most of mCherry positive cells were co-localized with neuronal marker NeuN (arrows).

Example 3—In Situ Conversion of Glial Cells into GABAergic Neurons Inside Brains AAV5 viral vectors were produced to express NeuroD1 and Dlx2. The AAV5 expressing NeuroD1 and Dlx2 viral vectors were injected into R6/2 mice, a mouse model for Huntington's disease. Following injection of AAV5 expressing NeuroD1 and Dlx2, astrocytes of the striatum generated new neurons in the Huntington's disease model R6/2 mice (FIGS. 14A-F). Most of the NeuroD1+Dlx2 converted neurons were GABAergic neurons (FIGS. 15A-B).

Figure 17:
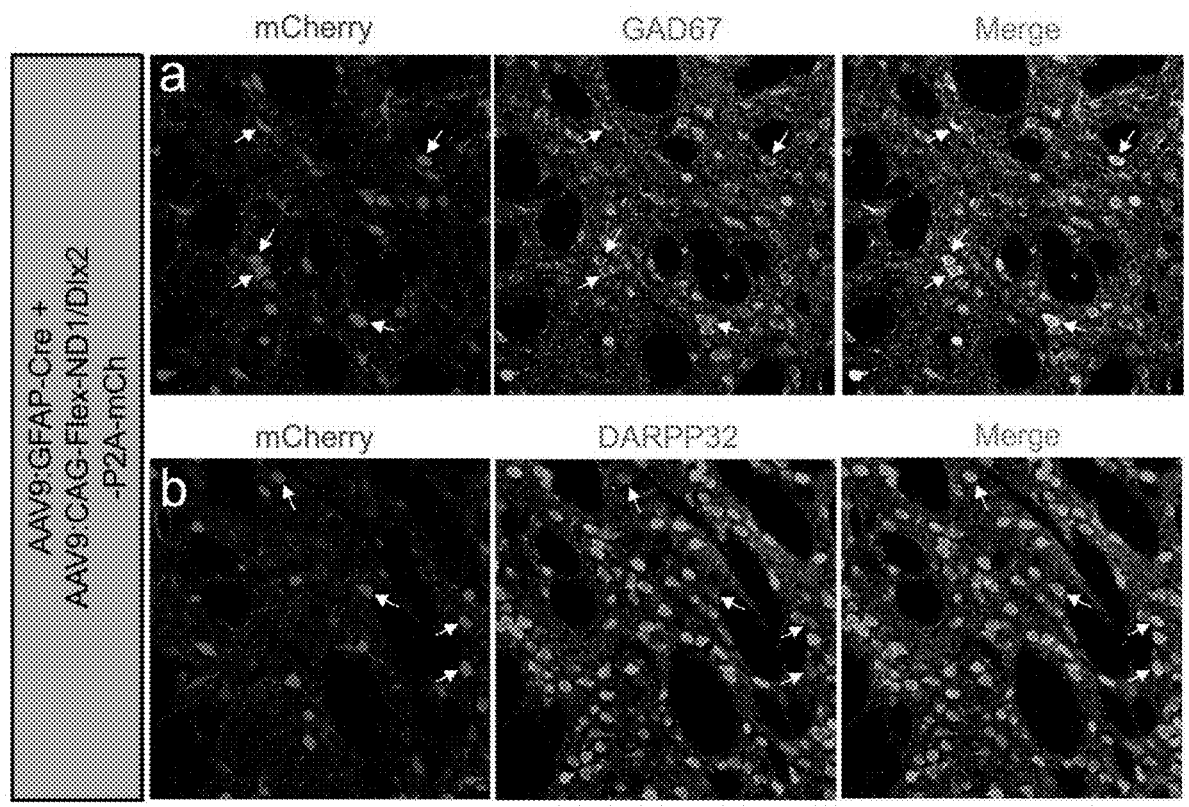
FIG. 17A-B. Characterization of glia-converted neurons in the striatum by AAV9. (A) NeuroD1/Dlx2 converted neurons were immuno-positive for GABAergic neuronal marker GAD67 (arrows). (B) Some of the converted neurons also were immuno-positive for DARPP32 (arrows), a marker for striatal GABAergic medium spiny neurons.

In addition to AAV5 viral vectors, the capability of AAV9 viral vectors for in vivo cell conversion was confirmed. An AAV9 viral vector was used to express NeuroD1 and Dlx2 in astrocytes under the control of astrocyte promoter GFAP. The AAV9 viral vectors expressing NeuroD1 and Dlx2 were able to convert astrocytes into neurons (FIG. 16A-D). Furthermore, immunostaining with a GABAergic neuron marker (GAD67) demonstrated that the majority of NeuroD1/Dlx2-converted neurons were GABAergic neurons (FIG. 17A-B). Among the GABAergic neurons, some of the NeuroD1/Dlx2-converted neurons were DARPP32-positive medium spiny neurons, which are often vulnerable in Huntington's disease. These results demonstrate that adeno-associated viral vectors such as AAV5 or AAV9 can be designed to express NeuroD1 and Dlx2 and that such designed vectors can be used to convert glial cells into GABAergic neurons, including DARPP32-positive medium spiny neurons, thereby treating Huntington's disease.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for forming GABAergic neurons in a striatum of a living mammal's brain from astrocytes, wherein said method comprises administering a nucleic acid sequence encoding a NeuroD1 polypeptide and a nucleic acid sequence encoding a Dlx2 polypeptide to said astrocytes within said striatum, wherein said nucleic acid sequence encoding said NeuroD1 polypeptide is operably linked to an astrocyte promoter sequence, wherein said NeuroD1 polypeptide and said Dlx2 polypeptide are expressed by said astrocytes, wherein said astrocytes form said GABAergic neurons within said striatum that are DARPP32-positive and functionally integrated into said living mammal's brain, and wherein said administration comprises a direct injection into said striatum of said living mammal's brain.

2. The method of claim 1, wherein said mammal is a human.

3. The method of claim 1, wherein said NeuroD1 polypeptide is a human NeuroD1 polypeptide or wherein said Dlx2 polypeptide is a human Dlx2 polypeptide.

4. The method of claim 1, wherein said nucleic acid sequence encoding said NeuroD1 polypeptide or said nucleic acid sequence encoding said Dlx2 polypeptide is administered to said astrocytes in the form of a viral vector.

5. The method of claim 4, wherein said viral vector is an adeno-associated viral vector.

6. The method of claim 1, wherein said nucleic acid sequence encoding said NeuroD1 polypeptide and said nucleic acid sequence encoding said Dlx2 polypeptide are located on the same viral vector, and wherein said viral vector is administered to said astrocytes.

7. The method of claim 1, wherein said nucleic acid sequence encoding said NeuroD1 polypeptide and said nucleic acid sequence encoding said Dlx2 polypeptide are located on separate viral vectors, and wherein each of said separate viral vectors is administered to said astrocytes.

8. The method of claim 1, wherein said nucleic acid sequence encoding said Dlx2 polypeptide is operably linked to a constitutive promoter sequence.

9. The method of claim 8, wherein said constitutive promoter sequence is an astrocyte promoter sequence.

10. The method of claim 9, wherein said astrocyte promoter sequence is a glial fibrillary acidic protein (GFAP) promoter sequence.

11. The method of claim 1, wherein said astrocyte promoter sequence is a glial fibrillary acidic protein (GFAP) promoter sequence.

* * * * *

SEQUENCE LISTING

<160> NUMBER OF SEQ ID NOS: 2

<210> SEQ ID NO 1
<211> LENGTH: 356
<212> TYPE: PRT
<213> ORGANISM: Homo sapiens

<400> SEQUENCE: 1

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
```

```
            165                 170                 175
Ser Gln Pro Thr Thr Asn Leu Val Ala Gly Cys Leu Gln Leu Asn Pro
            180                 185                 190
Arg Thr Phe Leu Pro Glu Gln Asn Gln Asp Met Pro Pro His Leu Pro
            195                 200                 205
Thr Ala Ser Ala Ser Phe Pro Val His Pro Tyr Ser Tyr Gln Ser Pro
            210                 215                 220
Gly Leu Pro Ser Pro Pro Tyr Gly Thr Met Asp Ser Ser His Val Phe
225                 230                 235                 240
His Val Lys Pro Pro Pro His Ala Tyr Ser Ala Ala Leu Glu Pro Phe
                245                 250                 255
Phe Glu Ser Pro Leu Thr Asp Cys Thr Ser Pro Ser Phe Asp Gly Pro
                260                 265                 270
Leu Ser Pro Pro Leu Ser Ile Asn Gly Asn Phe Ser Phe Lys His Glu
            275                 280                 285
Pro Ser Ala Glu Phe Glu Lys Asn Tyr Ala Phe Thr Met His Tyr Pro
            290                 295                 300
Ala Ala Thr Leu Ala Gly Ala Gln Ser His Gly Ser Ile Phe Ser Gly
305                 310                 315                 320
Thr Ala Ala Pro Arg Cys Glu Ile Pro Ile Asp Asn Ile Met Ser Phe
                325                 330                 335
Asp Ser His Ser His His Glu Arg Val Met Ser Ala Gln Leu Asn Ala
                340                 345                 350
Ile Phe His Asp
        355

<210> SEQ ID NO 2
<211> LENGTH: 328
<212> TYPE: PRT
<213> ORGANISM: Homo sapiens

<400> SEQUENCE: 2

Met Thr Gly Val Phe Asp Ser Leu Val Ala Asp Met His Ser Thr Gln
1               5                   10                  15
Ile Ala Ala Ser Ser Thr Tyr His Gln His Gln Gln Pro Pro Ser Gly
                20                  25                  30
Gly Gly Ala Gly Pro Gly Gly Asn Ser Ser Ser Ser Ser Ser Leu His
            35                  40                  45
Lys Pro Gln Glu Ser Pro Thr Leu Pro Val Ser Thr Ala Thr Asp Ser
    50                  55                  60
Ser Tyr Tyr Thr Asn Gln Gln His Pro Ala Gly Gly Gly Gly Gly Gly
65                  70                  75                  80
Gly Ser Pro Tyr Ala His Met Gly Ser Tyr Gln Tyr Gln Ala Ser Gly
                85                  90                  95
Leu Asn Asn Val Pro Tyr Ser Ala Lys Ser Ser Tyr Asp Leu Gly Tyr
            100                 105                 110
Thr Ala Ala Tyr Thr Ser Tyr Ala Pro Tyr Gly Thr Ser Ser Ser Pro
        115                 120                 125
Ala Asn Asn Glu Pro Glu Lys Glu Asp Leu Glu Pro Glu Ile Arg Ile
    130                 135                 140
Val Asn Gly Lys Pro Lys Lys Val Arg Lys Pro Arg Thr Ile Tyr Ser
145                 150                 155                 160
Ser Phe Gln Leu Ala Ala Leu Gln Arg Arg Phe Gln Lys Thr Gln Tyr
                165                 170                 175
```

```
Leu Ala Leu Pro Glu Arg Ala Glu Leu Ala Ala Ser Leu Gly Leu Thr
            180                 185                 190

Gln Thr Gln Val Lys Ile Trp Phe Gln Asn Arg Arg Ser Lys Phe Lys
        195                 200                 205

Lys Met Trp Lys Ser Gly Glu Ile Pro Ser Glu Gln His Pro Gly Ala
    210                 215                 220

Ser Ala Ser Pro Pro Cys Ala Ser Pro Pro Val Ser Ala Pro Ala Ser
225                 230                 235                 240

Trp Asp Phe Gly Val Pro Gln Arg Met Ala Gly Gly Gly Gly Pro Gly
                245                 250                 255

Ser Gly Gly Ser Gly Ala Gly Ser Ser Gly Ser Ser Pro Ser Ser Ala
            260                 265                 270

Ala Ser Ala Phe Leu Gly Asn Tyr Pro Trp Tyr His Gln Thr Ser Gly
        275                 280                 285

Ser Ala Ser His Leu Gln Ala Thr Ala Pro Leu Leu His Pro Thr Gln
        290                 295                 300

Thr Pro Gln Pro His His His His His His His Gly Gly Gly Gly Ala
305                 310                 315                 320

Pro Val Ser Ala Gly Thr Ile Phe
                325
```